(12) United States Patent
Vogel et al.

(10) Patent No.: US 8,957,108 B2
(45) Date of Patent: Feb. 17, 2015

(54) USE OF 5,6-DIMETHYLXANTHENONE-4-ACETIC ACID AS AN ANTIVIRAL AGENT

(75) Inventors: Stefanie N. Vogel, Columbia, MD (US); Zachary J. Roberts, Baltimore, MD (US); Jorge Blanco, Washington, DC (US)

(73) Assignee: University of Maryland, Baltimore, Baltimore, MD (US)

( * ) Notice: Subject to any disclaimer, the term of this patent is extended or adjusted under 35 U.S.C. 154(b) by 126 days.

(21) Appl. No.: 13/047,385

(22) Filed: Mar. 14, 2011

(65) Prior Publication Data

US 2011/0218239 A1 Sep. 8, 2011

Related U.S. Application Data

(60) Division of application No. 11/937,129, filed on Nov. 8, 2007, now abandoned, which is a continuation-in-part of application No. 11/936,656, filed on Nov. 7, 2007, now abandoned.

(60) Provisional application No. 60/864,991, filed on Nov. 9, 2006.

(51) Int. Cl.
*A61K 31/35* (2006.01)
*A61K 31/44* (2006.01)
(Continued)

(52) U.S. Cl.
CPC ............ *A61K 31/353* (2013.01); *A61K 31/473* (2013.01)
USPC .......................................... 514/455; 514/290

(58) Field of Classification Search
CPC ...................................................... A61K 31/352
USPC .................................................... 514/455, 290
See application file for complete search history.

(56) References Cited

U.S. PATENT DOCUMENTS

| 5,281,620 A | 1/1994 | Denny et al. |
|---|---|---|
| 5,629,322 A | 5/1997 | Guthikonda et al. |
| 5,710,134 A | 1/1998 | Boslet et al. |

(Continued)

FOREIGN PATENT DOCUMENTS

| JP | 2005194259 | * 7/2005 |
|---|---|---|
| WO | WO 0103681 | 1/2001 |

OTHER PUBLICATIONS

Siren et al. "Cytokine and contact-dependent activation of natural killer cells by influenza A or sendai virus-infected macrophages," Journal of General Virology, 2004, vol. 85, pp. 2357-2364.*

(Continued)

*Primary Examiner* — Shengjun Wang
(74) *Attorney, Agent, or Firm* — Evans & Molinelli PLLC; Eugene J. Molinelli

(57) ABSTRACT

The invention relates to the areas of therapeutics, pharmaceuticals, drug discovery, and immunotherapy. More specifically, the present invention relates to methods of stimulating the immune system through the administration of flavone acetic acid [FAA] analogs, and in particular, the flavone acetic acid analog, 5,6-dimethylxanthenone-4-acetic acid (DMXAA) so as to comprise an antimicrobial therapeutic agent for the treatment of viral infections of DNA and RNA viruses in humans and non-human animals. The invention is especially suitable for use in a process of treating and preventing infection by, for example, rhinoviruses, enteroviruses, and influenza viruses.

7 Claims, 9 Drawing Sheets

(51) Int. Cl.
  *A61K 31/353* (2006.01)
  *A61K 31/473* (2006.01)

(56) References Cited

U.S. PATENT DOCUMENTS

| | | | |
|---|---|---|---|
| 5,821,261 A | 10/1998 | Durette et al. | |
| 5,866,612 A | 2/1999 | Oplinger et al. | |
| 5,889,056 A | 3/1999 | Hodson et al. | |
| 5,908,842 A | 6/1999 | Guthikonda et al. | |
| 5,972,975 A | 10/1999 | Esser et al. | |
| 5,977,077 A | 11/1999 | Winter et al. | |
| 6,043,358 A | 3/2000 | Caldwell et al. | |
| 6,071,509 A * | 6/2000 | Hellstrand et al. | 424/85.2 |
| 6,090,846 A | 7/2000 | Oplinger et al. | |
| 6,225,305 B1 | 5/2001 | Oplinger et al. | |
| 6,274,611 B1 | 8/2001 | Critchfield et al. | |
| 6,297,276 B1 | 10/2001 | Oplinger et al. | |
| RE37,438 E | 11/2001 | Oplinger et al. | |
| 6,355,689 B1 | 3/2002 | Beswick et al. | |
| 6,369,272 B1 | 4/2002 | Beams et al. | |
| 6,372,733 B1 | 4/2002 | Caldwell et al. | |
| 6,399,654 B1 | 6/2002 | Lin et al. | |
| 6,495,585 B2 | 12/2002 | Bellnier et al. | |
| 6,495,606 B1 | 12/2002 | Beswick et al. | |
| 6,620,848 B2 | 9/2003 | Beams et al. | |
| 6,667,337 B2 | 12/2003 | Wilson | |
| 6,869,975 B2 | 3/2005 | Abe et al. | |
| 6,894,071 B2 | 5/2005 | Nuijen et al. | |
| 7,087,627 B1 | 8/2006 | Davis | |
| 7,105,501 B2 | 9/2006 | Davis | |
| 7,115,557 B2 | 10/2006 | Olmarker | |
| 7,166,640 B2 | 1/2007 | Berg | |
| RE39,576 E | 4/2007 | Hodson et al. | |
| 7,317,040 B2 | 1/2008 | Box et al. | |
| 7,344,710 B2 | 3/2008 | Dang et al. | |
| 2004/0053955 A1 | 3/2004 | Iwanowicz et al. | |
| 2005/0049273 A1 | 3/2005 | Bastow et al. | |
| 2005/0089509 A1 | 4/2005 | Arulanandam et al. | |
| 2006/0198846 A1 | 9/2006 | Davis | |
| 2009/0042991 A1 | 2/2009 | Barsoum et al. | |

OTHER PUBLICATIONS

Kos et al. "Role of natural killer cells in the generation of influenza virus-specific cytotoxic T cells," Cellular Immunology, 1996, vol. 173, pp. 1-6.*
JP 2005194259 translation, 2005.*
Aitken, R.A. et al. (1996) "Synthesis and Antitumor Activity of New Derivatives of Flavone-8-Acetic Acid (FAA). Part 1: 6-Methyl Derivatives," Arch. Pharm. 329(11): 489-497 (Abstract only).
Aitken, R.A. et al. (1997) "Synthesis and Antitumor Activity of New Derivatives of Flavone-8-Acetic Acid (FAA). Part 2: Ring-Substituted Derivatives," Arch. Pharm. 330(7):215-224 (Abstract only).
Aitken, R.A. et al. (1998) "Synthesis and Antitumor Activity of New Derivatives of Flavone-8-Acetic Acid (FAA). Part 3: 2-Heteroaryl Derivatives," Arch. Pharm. 331(12):405-411 (Abstract Only).
Aitken, R.A. et al. (2000) "Synthesis and Antitumor Activity of New Derivatives of Flavone-8-Acetic Acid (FAA). Part 4: Variation of the Basic Structure," Arch. Pharm. 333(6):181-188 (Abstract only).
Akira, S. et al. (2006) "Pathogen Recognition and Innate Immunity," Cell, 2006, 124:783-801.
Baguley, B.C., (2001) "Small-Molecule Cytokine Inducers Causing Tumor Necrosis," Curr. Opin. Investig. Drugs 2(7):967-975.
Biron, C.A. (1998) "Role of Early Cytokines, Including Alpha and Beta Interferons (IFN-Alpha/Beta) In Innate and Adaptive Immune Responses to Viral Infections," Semin. Immunol., 1998, 10:383-390.
Dobrovolskaia, M.A. et al. (2003) "Induction of In Vitro Reprogramming by Toll-Like Receptor (TLR) 2 and TLR4 Agonists in Murine Macrophages: Effects of TLR "Homotolerance" Versus "Heterotolerance" on NF-Kappa B Signaling Pathway Components," J. Immun. 170:508-519.
Dornand et al. (2004) ("Impairment of Intramacrophagic *Brucella suis* Multiplication by Human Natural Killer Cells Through a Contact Dependent Mechanism," Infect. Immun. 72(4):2303-2311.

Friedman, R.M. (1977) "Antiviral Activity of Interferons," Bacteriological Reviews, 41(3):543-567.
Gobbi, S. et al. (2006) "New Derivatives of Xanthenone-4-Acetic Acid: Synthesis, Pharmacological Profile and Effect on TNF-Alpha and NO Production in Human Immune Cells," Bioorg. Med. Chem. 14(12):4101-4109.
Hemmi, H. et al. (2002) "Small Anti-Viral Compounds Activate Immune Cells Via the TLR7 MyD88-Dependent Signaling Pathway," Nature Immunology 3:196-200.
Iwamura, T. et al. (2001) "Induction of IRF-3/-7 Kinase and NF-KappaB in Response to Double-Stranded RNA and Virus Infection: Common and Unique Pathways," Genes and Cells 6:375-388.
Johnson, C. L. et al. (2006) "Card Games Between Virus and Host Get a New Player," Trends Immunol. 27:1-4.
Kato, H. et al. (2006) "Differential Roles of MDA5 and RIG-1 Helicases in the Recognition of RNA Viruses," Nature 441:101-105.
Kawai, T. et al. (1999) "Unresponsiveness of MyD88-Deficient Mice to Endotoxin," Immunity 11:115-122.
Kopp, E. et al. (1994) "Inhibition of NF-Kappa B by Sodium Salicylate and Aspirin," Science 265:956-959.
Levy, D.E. et al. (2001) "The virus battles: IFN induction of the antiviral state and mechanisms of viral evasion," Cytokine Growth Factor Rev. 12:143-156.
Medvedev, A. E. et al. (2000) "Inhibition of Lipopolysaccharide-Induced Signal Transduction in Endotoxin-Tolerized Mouse Macrophages: Dysregulation of Cytokine, Chemokine, and Toll-Like Receptor 2 and 4 Gene Expression," J. Immunol. 164:5564-5574.
Perera, P.-Y. et al. (1994) "Activation of LPS-Inducible Genes by the Antitumor Agent 5,6-Dimethylxanthenone-4-Acetic Acid in Primary Murine Macrophages; Dissection of Signaling Pathways Leading to Gene Induction and Tyrosine Phosphorylation," J. Immunol. 153(10):4684-4693.
Pfeffer, L.M. et al. (1998) "Biological Properties of Recombinant Alpha-Interferons: 40th Anniversary of the Discovery of Interferons," Cancer Research 58(12):2489-2499.
Philpott, M. et al. (2001) "The Antitumor Agent 5,6-Dimethylxanthenone-4-Acetic Acid Acts In Vitro on Human Mononuclear Cells as a Co-Stimulator With Other Inducers of Tumor Necrosis Factor," Eur. J. Cancer 37:1930-1937.
Philpott, M. et al., "Production of Tumor Necrosis Factor Alpha by Cultured Human Peripheral Blood Leucocytes in Response to the Anti-Tumor Agent 5,6-Dimethylxanthenone-4-Acetic Acid (NSC 640488)," Br. J. Cancer, 1997, 76(12): 1586-1591.
Roberts, Z.J. et al. (2007) "The Chemotherapeutic Agent DMXAA Potently and Specifically Activates the TBK1-IRF-3 Signaling Axis," J. Exp. Med. 204(7):1559-1569.
Schafer, S.L. et al. (1998) "Regulation of Type 1 Interferon Gene Expression by Interferon Regulatory Factor-3," J. Biol. Chem. 273:2714-2720.
Sen, G.C. et al. (1992) "The Interferon System. A Bird's Eye View of Its Biochemistry," J. Biol. Chem. 267(8):5017-5020.
Stark, G.R. et al. (1998) "How Cells Respond to Interferons," Annu. Rev. Biochem. 67:227-264.
Toshchakov, V. et al. (2002) "TLR4, But Not TLR2, Mediates IFN-Beta-Induced STAT1alpha/beta-Dependent Gene Expression in Macrophages," Nature Immunology 3:392-398.
Vogel, S. N. et al. (2003) "TLRs: Differential Adapter Utilization by Toll-Like Receptors Mediates TLR-Specific Patterns of Gene Expression," Molecular Intervention 3:466-477.
Vogel, S.N. et al. (1987) "Macrophages From Endotoxin-Hyporesponsive (Lpsd) C3HfHej Mice Are Permissive for Vesicular Stomatitis Virus Because of Reduced Levels of Endogenous Interferon: Possible Mechanism for Natural Resistance to Virus Infection," J. Virol. 61(3):812-818.
Weinstein, S. L. et al. (2000) "Phosphatidylinositol 3-Kinase and mTOR Mediate Lipopolysaccharide-Stimulated Nitric Oxide Production in Macrophages Via Interferon-Beta," J. Leukocyte Biol. 67:405-414.
Yamamoto, M. et al. (2002) "Cutting Edge: A Novel Toll/IL-1 Receptor Domain-Containing Adapter That Preferentially Activates the IFN-Beta Promoter in the Toll-Like Receptor Signaling," J. Immunol. 169:6668-6672.

(56) References Cited

OTHER PUBLICATIONS

Yin, M. J. et al. (1998) "The Anti-Inflammatory Agents Aspirin and Salicylate Inhibit the Activity of I(Kappa)B Kinase-Beta," Nature 396:77-80.
Yoneyama, M. et al. (2004) "The RNA Helicase RIG-1 Has an Essential Function in Double-Stranded RNA-Induced Innate Antiviral Responses," Nature Immunology 5:730-737.
Zhou et al. (2002) "5,6-Dimethylxanthenone-4-Acetic Acid (DMXM): A New Biological Response Modifier for Cancer Therapy," Invest. New Drugs 20(3):281-295.
Baguley, B.C. et al. (1997) "Immunomodulatory Actions of Xanthenone Anticancer Agents," BioDrugs. 8(2):119-127.
Baguley, B.C. et al. (2002) "DMXAA: An Antivascular Agent With Multiple Host Responses," Int. J. Radiat. Oncol. Biol. Phys. 54(5):1503-1511.
Baguley, B.C. et al. (2003) "Antivascular Therapy of Cancer: DMXAA," Lancet Oncology 4:141-148.
Ching, L.M. et al. (1987) "Induction of Natural Killer Cell Activity by the Antitumour Compound Flavone Acetic Acid (NSC 347 512)," Eur. J. Cancer Clin. Oncol. 23(7):1047-1050.
Ching, L.M. et al. (1989) "Reduction of Cytotoxic Effector Cell Activity in Colon 38 Tumours Following Treatment with Flavone Acetic Acid," Eur. J. Cancer Clin. Oncol. 25(7):1061-1065.
Ching, L.M. et al. (1999) "Induction of Intratumoral Tumor Necrosis Factor (TNF) Synthesis and Hemorrhagic Necrosis by 5,6-Dimethylxanthenone-4-Acetic Acid (DMXAA) in TNF Knockout Mice," Cancer Res. 59:3304-3307.
Damia, G. et al. (1990) "Flavone Acetic Acid Antitumour Activity Against a Mouse Pancreatic Adenocarcinoma Is Mediated by Natural Killer Cells," Cancer Immunol. Immunother. 32:241-244.
Diana, J. et al. (2009) "NKT cells: Friend or foe during viral infections?," Eur. J. Immunol. 39:3283-3291.
Hsu, J. et al. (2012) "Antivirals for Treatment of Influenza," Annals Internal Med. 156(7):512-524.
Joseph, W.R. et al. (1999) "Stimulation of Tumors to Synthesize Tumor Necrosis Factor-α in Situ Using 5,6-Dimethylxanthenone-4-acetic Acid: A Novel Approach to Cancer Therapy," Cancer Res. 59:633-638.
Liang-Chuan, S. et al. (2004) "Induction of Tumour Necrosis Factor and Interferon-γ in Cultured Murine Splenocytes by the Antivascular Agent DMXAA and Its Metabolites," Biochemical Pharmacology 67:937-945.
Pang, J-H, et al. (1998) "Antitumour Activity of the Novel Immune Modulator 5,6-Dimethylxanthenone-4-Acetic Acid (DMXAA) in Mice Lacking the Interferon-Gamma Receptor," Eur. J. Cancer 34:1282-1289.
Pratesi, G. et al. (1990) "Role of T Cells and Tumour Necrosis Factor in Antitumour Activity and Toxicity of Flavone Acetic Acid," Eur. J. Cancer 26(1):1079-1083.
Roberts, Z.J. et al. (2008) "IFN-Beta-Dependent Inhibition of Tumor Growth by the Vascular Disrupting Agent 5,6-Dimethylxanthenone-4-Acetic Acid (DMXAA)," J. Interferon Cytokine Res. 28(3):133-139.
Shirey, K.A. et al. (2011) "The Anti-Tumor Agent, 5,6-Dimethylxanthenone-4-Acetic Acid (DMXAA), Induces IFN-β-Mediated Antiviral Activity In Vitro and In Vivo," J. Leukoc. Biol. 89(3):351-357.
Zhou, L. et al. (2002b) "The Antitumour Activity of 05,6-Dimethylxanthenone-4-Acetic Acid (DMXAA) in TNF Receptor-1 Knockout Mice," Br. J. Cancer 87:465-470.
Zwi, L.J. et al. (1990) "Necrosis in Non-Tumour Tissues Caused by Flavone Acetic Acid and 5,6-Dimethyl Xanthenone Acetic Acid," Br. J. Cancer 62:932-934.

Ahlenstiel et al. (2011) "Early Changes in Natural Killer Cell Function Indicate Virologic Response to Interferon Therapy for Hepatitis C," Gastroenterology 141:1231-1239.
Amadei et al. (2010) "Activation of Natural Killer Cells During Acute Infection With Hepatitis C Virus," Gastroenterology 138: 1536-1545.
Anonymous; Genetic Engineer. News (2010) "Antisoma and Novartis Ditch ASA404 After Second Phase III NSCLC Trial Bombs," Genetic Engineer. News http://www.genengnews.com/gen-news-highlights/antisoma-and-novartis-ditch-asa404-af; pp. 1-3.
Beli et al. (2011) "Natural killer cell function is altered during the primary response of aged mice to influenza infection," Mechanisms of Ageing and Development 132:503-510.
Cheng, G. et al. (2011) "Pharmacologic Activation of the Innate Immune System to Prevent Respiratory Viral Infections," Amer. J. Respir. Cell. Mol. Biol. 45:480-488.
Claus (2010) "Evaluation of Human Natural Killer Cell Activities in Whole Blood," Current Protocols in Immunology 91:7.39.1-17 (17 pages).
Crawford, L.V. (1973) "Proteins of Polyoma Virus," Br. Med. Bull. 29(3):253-258.
Du, N. (2010) "Differential Activation of NK Cells by Influenza A Pseudotype H5N1 and 1918 and 2009 Pandemic H1N1 Viruses," J. Virol. 84(15):7822-7831.
Gerosa, F. et al. (2005) "The Reciprocal Interaction of NK Cells with Plasmacytoid or Myeloid Dendritic Cells Profoundly Affects Resistance Functions," J Immunol 174:727-734.
Green, M. (1970) "Oncogenic Viruses," Ann. Rev. Biochem. 39:701-756.
Ishikawa, H. et al. (2010) "IFN-γ Production Downstream of NKT Cell Activation in Mice Infected With Influenza Virus Enhances the Cytolytic Activities of Both NK Cells and Viral Antigen-Specific CD8 T cells," Virology 407:325-332.
Li, F. et al. (2011) "Natural Killer Cells Are Involved in Acute Lung Immune Injury Caused by Respiratory Syncytial Infection," J. Virol. 86(4):2251-2258.
McKeage et al. (2008) "Randomised Phase II Study of ASA404 Combined With Carboplatin and Paclitaxel in Previously Untreated Advanced Non-Small Cell Lung Cancer," Brit. J. Canc. 99(12):2006-2012.
Miller, Jeffrey S. (2002) "Biology of Natural Killer Cells in Cancer and Infection," Cancer Investigation 20(3):405-419.
Neff-LaFord, H.D. et al. (2003) "Fewer CTL, Not Enhanced NK cells, Are Sufficient for Viral Clearance From the Lungs of Immunocompromised Mice," Cellular Immunology 226 54-64.
Renneson, Joelle (2011) "A Detrimental Role for Invariant Natural Killer T Cells in the Pathogenesis of Experimental Dengue Virus Infection," The American Journal of Pathology vol. 179(4):1873-1883.
Shereck, E. et al. (2007) "Human Natural Killer Cells in Health and Disease," Pediatr. Blood Cancer 49:615-623.
Yoon, JJ.C. et al. (2011) "Cell-to-Cell Contact with Hepatitis C Virus-Infected Cells Reduces Functional Capacity of Natural Killer Cells," J. Virol. 85(23):12557-12569.
Young, H. (2010) "Editorial: One Small Molecule: A New Way to Treat the Flu?," J. Leuk. Biol. 89:327-328.
Zhang et al. (2010) "Anti-West Nile Virus Activity of In Vitro Expanded Human Primary Natural Killer Cells,"BMC Immunology 113:1-9.
Zhao (2011) "Differential Modulating Effect of Natural Killer (NK) T Cells on Interferon-γ Production and Cytotoxic Function of NK Cells and Its Relationship With NK Subsets in Chlamydia muridarum Infection," Immunology 134:172-184.

* cited by examiner

FIG. 3A, 3B, and 3C
A
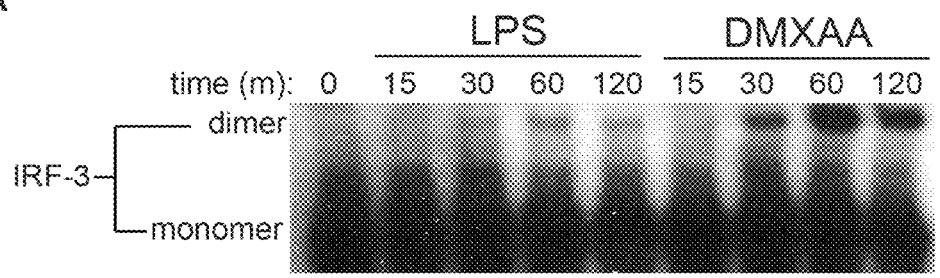
B
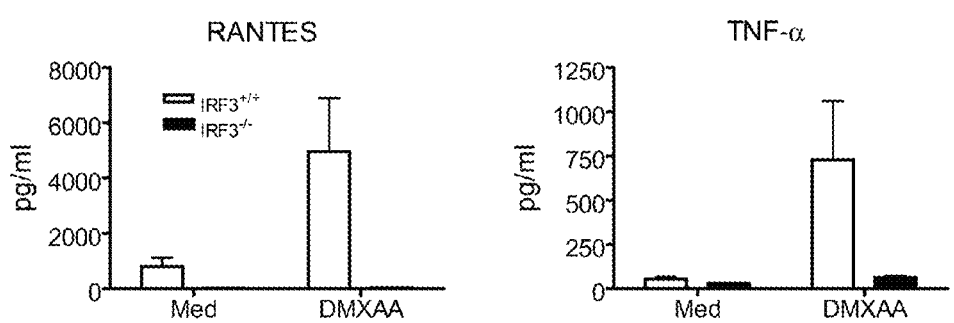
C
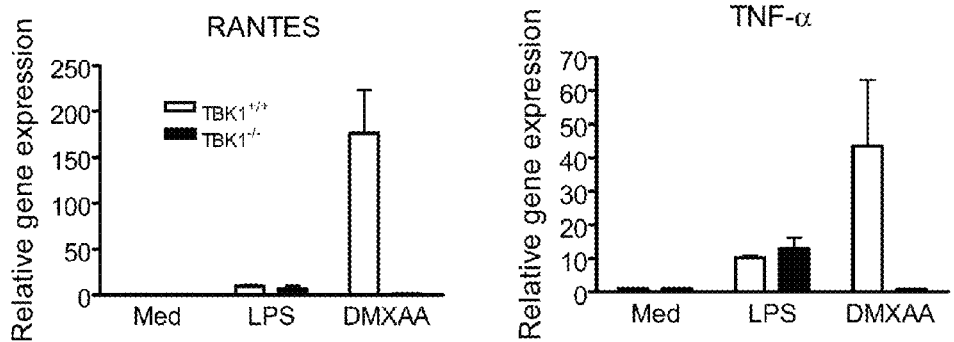

USE OF 5,6-DIMETHYLXANTHENONE-4-ACETIC ACID AS AN ANTIVIRAL AGENT

CROSS-REFERENCE TO RELATED APPLICATIONS

This application is a divisional application of U.S. patent application Ser. No. 11/937,129 (filed on Nov. 8, 2007, pending), which application is a continuation-in-part of U.S. patent application Ser. No. 11/936,656 (filed on Nov. 7, 2007, abandoned), which applications claim priority to U.S. Patent Application Ser. No. 60/864,991 (filed on Nov. 9, 2006), all of which applications are herein incorporated by reference in their entireties.

STATEMENT AS TO RIGHTS TO INVENTIONS MADE UNDER FEDERALLY SPONSORED RESEARCH OR DEVELOPMENT

This invention was made with U.S. Government support under Grant No. AI18797, awarded by the National Institutes of Health. The U.S. Government has certain rights in this invention.

FIELD OF THE INVENTION

The present invention relates to the areas of therapeutics, pharmaceuticals, drug discovery, and immunotherapy. More specifically, the present invention relates to methods of stimulating the immune system through the administration of flavone acetic acid analogues, and in particular, the flavone acetic acid analogue, 5,6-dimethylxanthenone-4-acetic acid (DMXAA) so as to comprise an antimicrobial therapeutic agent for the treatment of viral, fungal, bacterial or parasitic infections in humans and non-human animals. The invention is especially suitable for use in a process of treating and preventing infection by viruses (for example, rhinoviruses, enteroviruses, and influenza viruses, etc.) and bacteria (especially intracellular bacterial pathogens such as *Francisella tularensis*).

BACKGROUND OF THE INVENTION

The innate immune response in a human or mammal clears the infection and/or provides prophylactic protection against pathogenic challenge. The innate immune response is a nonspecific immune response generated by the host in response to infection by pathogenic organisms. It is independent of T cells, and occurs very rapidly after infection. The principal cells involved in mounting an innate immune response include the cells of the mononuclear phagocyte system (e.g. macrophages), granulocytes, and natural killer (NK) cells. Macrophages function in innate immunity to phagocytose and degrade foreign particles; secrete enzymes, reactive oxygen species, nitric oxide, and lipid-derived mediators (e.g. prostaglandins) which serve to kill pathogenic organisms and control the spread of infection; and produce cytokines that recruit other inflammatory cells to the site of infection, such as neutrophils. Granulocytes include neutrophils, eosinophils, and basophils, and are important in generating an inflammatory response. Natural Killer cells are a subset of lymphocytes that do not require prior contact with an antigen to become cytotoxic, but rather are activated by stimulation from cytokines such as type I IFN, IFN-γ, IL-12, TNF or IL-2.

Upon infection by a pathogenic organism, one of the first cellular responses is increased transcription of IRF-3 in the infected cell(s), which results in increased production of type I IFN (e.g. IFN-α and IFN-β). IFN-β acts in a paracrine fashion on neighboring cells to cause them to produce IFN-γ, which in turn acts on macrophages, resulting in their activation. Activated macrophages produce more cytokines, have increased microbicidal activity, and participate in the specific immune response by presenting antigens to lymphocytes. Type I IFNs also increase the expression of iNOS, an enzyme responsible for generating nitric oxide (NO), which is toxic to pathogens. Additionally, type I IFNs increase the lytic activity of NK cells, and help to recruit them to the site of infection.

Traditionally, bacterial infections have been treated through the use of various antibiotics, which usually comprise chemical compounds that are either toxic to the bacteria or interfere with bacterial metabolism sufficiently that growth is inhibited and/or killing occurs. However, bacteria evolve very rapidly, and are capable of transferring antibiotic resistance across species. This has resulted in an increased resistance among bacteria to traditional antibiotics. Therapy of viral infections has been modeled after that of bacterial infections. However, application of the principles of antibacterial therapy to antiviral therapy (and prophylaxis) presents a number of unique problems. A major challenge is identifying antiviral compounds that are relatively non-toxic to mammalian cells because, unlike bacteria, viruses must replicate intracellularly and often employ host cell biomolecules and organelles for the synthesis of virus particles. Consequently, antiviral agents are available to treat only a few viral diseases because any drug that interferes significantly with viral replication is likely to be toxic to the host.

Accordingly, a need remains for effective antibacterial agents that can avoid bacterial mechanisms of resistance, as well as for safe and effective antiviral agents with a broad spectrum of antiviral activity and reduced toxicity to the host.

Flavonoids, which are found ubiquitously in photosynthesizing plant cells, induce biologic effects in humans and other animals, ranging from the induction of cytokines such as interferon gamma (IFN-γ) in lymphocytes to the inhibition of a number of key metabolic regulatory enzymes. Because of the potential therapeutic effects of flavonoids, and their low toxicity profile in experimental animals, several synthetic flavonoids have been screened for antitumor activity (see, e.g., U.S. Pat. No. 5,126,129), antiviral activity (see, e.g., U.S. Pat. Nos. 6,274,611; 6,399,654 and 7,166,640; WO 01/03681), and antiparasitic activity (see, e.g., U.S. Pat. No. 5,977,077).

Flavone acetic acid analogues (FAA) comprise a class of flavonoids. DMXAA (5,6-dimethylxanthenone-4-acetic acid) is an analogue of flavone acetic acid (FAA) and, like FAA, causes the ischemic hemorrhagic necrosis of solid tumors in mice. Additionally, FAA and DMXAA both induce the synthesis of tumor necrosis factor alpha (TNF-α), stimulates the production of nitric oxide, and activates macrophages to be tumoricidal. However, DMXAA is more effective and 12-fold more potent in vivo against murine colon tumors than FAA, and DMXAA induces cytokine production in both human and murine cell lines, whereas FAA acts on human cells in vitro but does not exert anti-tumor effects in humans in vivo and has undesirable side effects. For example, DMXAA has been shown to induce the production of TNF-α mRNA in the myelomonocytic human cell line HL-60 and in human peripheral blood leukocytes (Aitken et al. (1996) "Synthesis And Antitumor Activity Of New Derivatives Of Flavone-8-Acetic Acid (FAA). Part 1: 6-Methyl Derivatives," Arch. Pharm. (Weinheim) 329(11):489-497; Aitken et al. (1997) "Synthesis And Antitumor Activity Of New Derivatives Of Flavone-8-Acetic Acid (FAA). Part 2: Ring-Substituted Derivatives," Arch. Pharm. (Weinheim) 330(7):215-224; Aitken et al. (1998) "Synthesis and antitumor activity of new derivatives of flavone-8-acetic acid (FAA). Part 3: 2-Heteroaryl derivatives," Arch. Pharm. (Weinheim) 331(12): 405-411; Aitken et al. (2000) "Synthesis And Antitumor Activity Of New Derivatives Of Flavone-8-Acetic Acid (FAA). Part 4: Variation Of The Basic Structure," Arch. Pharm. (Weinheim) 333(6):181-188; Baguley, B. C. (2001) "Small-Molecule Cytokine Inducers Causing Tumor Necrosis", Curr. Opin. Investig. Drugs 2(7):967-975; Gobbi et al. (2006) "New Derivatives Of Xanthenone-4-Acetic Acid: Synthesis, Pharmacological Profile And Effect On TNF-Alpha And NO Production In Human Immune Cells," Bioorg. Med. Chem. 14(12):4101-4109; Philpott et al. (1997) "Production Of Tumor Necrosis Factor Alpha By Cultured Human Peripheral Blood Leucocytes In Response To The Anti-Tumor Agent 5,6-Dimethylxanthenone-4-Acetic Acid (NSC 640488)," Br. J. Cancer 76(12):1586-1591; Zhou et al. (2002) "5,6-Dimethylxanthenone-4-Acetic Acid (DMXAA): A New Biological Response Modifier For Cancer Therapy," Invest. New Drugs 20(3):281-295).

Thus, despite all previous efforts, a need remains for improved antimicrobial agents. The present invention is directed to this and other goals.

SUMMARY OF THE INVENTION

The present invention relates to the areas of therapeutics, pharmaceuticals, drug discovery, and immunotherapy. More specifically, the present invention relates to methods of stimulating the immune system through the administration of flavone acetic acid [FAA] analogues, and in particular, the flavone acetic acid analogue, 5,6-dimethylxanthenone-4-acetic acid (DMXAA) so as to provide an antimicrobial therapeutic agent for the treatment of viral, fungal, bacterial or parasitic infections in humans and non-human animals. The invention is especially suitable for use in a process of treating and preventing infection by viruses (for example, rhinoviruses, enteroviruses, and influenza viruses, etc.) and bacteria (especially intracellular bacterial pathogens such as *Francisella tularensis*).

In detail, the invention provides a method of treating or preventing an infection in a mammal comprising administering to a mammal in need of such treatment a pharmacologically acceptable, therapeutically effective amount of a compound of formula (I):

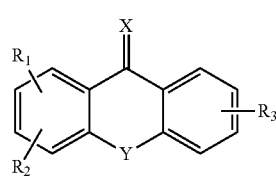

Formula (I)

or a pharmaceutically acceptable salt or ester thereof with a pharmaceutically acceptable acid;
wherein:

X and Y are O or N, and $R_1$, $R_2$, and $R_3$ are each independently chosen from H, $C_1$-$C_6$ alkyl, halogen, $CF_3$, CN, $NO_2$, $NH_2$, OH, OR, NHCOR, $NHSO_2R$, SR, $SO_2R$, $CH_2COOH$, or NHR, wherein each R is independently $C_1$-$C_6$ alkyl optionally substituted with one or more substituents selected from hydroxy, amino, ethoxy, and methoxy, and each of $R_1$, $R_2$, and $R_3$ may be present at any one of the available carbon positions 1 to 8; and in each of the carbocyclic aromatic rings in formula (I), up to two of the methine (—CH=) groups may be replaced by an aza (—N=) group; and any two of $R_1$, $R_2$, and $R_3$ may additionally together represent the group —CH=CH—CH=CH—, such that this group, together with the carbon or nitrogen atoms to which it is attached, forms a fused six membered aromatic ring.

The invention further provides the embodiment of the above-described method wherein the FAA analogue is DMXAA (5,6-dimethylxanthenone-4-acetic acid).

The invention further provides the embodiment of the above-described method wherein the infection is caused by a bacterial pathogen (especially an intracellular bacterial pathogen), or a viral pathogen (e.g., a DNA or RNA virus).

The invention further provides the embodiment of the above-described methods wherein the method is a method of treatment (i.e. a therapeutic method).

The invention further provides the embodiment of the above-described methods wherein the method is a method of prevention of infection (i.e. a prophylactic method).

The invention further provides the embodiment of the above-described methods wherein the compound is administered in conjunction with a second therapeutic agent.

The invention additionally provides a pharmaceutical composition comprising an amount of a compound of formula (I):

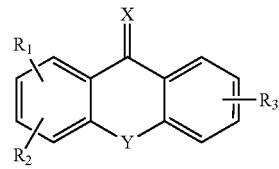

Formula (I)

or a pharmaceutically acceptable salt or ester thereof with a pharmaceutically acceptable acid;
wherein:

X and Y are O or N, and $R_1$, $R_2$, and $R_3$ are each independently chosen from H, $C_1$-$C_6$ alkyl, halogen, $CF_3$, CN, $NO_2$, $NH_2$, OH, OR, NHCOR, $NHSO_2R$, SR, $SO_2R$, $CH_2COOH$, or NHR, wherein each R is independently $C_1$-$C_6$ alkyl optionally substituted with one or more substituents selected from hydroxy, amino, ethoxy, and methoxy, and each of $R_1$, $R_2$, and $R_3$ may be present at any one of the available carbon positions 1 to 8; and in each of the carbocyclic aromatic rings in formula (I), up to two of the methine (—CH=) groups may be replaced by an aza (—N=) group; and any two of $R_1$, $R_2$, and $R_3$ may additionally together represent the group —CH=CH—CH=CH—, such that this group, together with the carbon or nitrogen atoms to which it is attached, forms a fused six membered aromatic ring;

and one or more pharmaceutically acceptable carriers, diluents or excipients.

The invention further provides the embodiment of the above-described pharmaceutical composition wherein the FAA analogue is DMXAA (5,6-dimethylxanthenone-4-acetic acid).

The invention further provides the embodiment of the above-described pharmaceutical composition wherein the infection is caused by a bacterial pathogen (especially an intracellular bacterial pathogen), or a viral pathogen (e.g., a DNA or RNA virus).

The invention further provides the embodiment of the above-described pharmaceutical compositions wherein the composition is provided to treat an existing infection (i.e. a therapeutic pharmaceutical composition).

The invention further provides the embodiment of the above-described pharmaceutical compositions wherein the composition is provided to prevent an anticipated infection (i.e. a prophylactic pharmaceutical composition).

The invention further provides the embodiments of the above-described pharmaceutical compositions wherein the compound is administered in conjunction with a second therapeutic agent.

A further object of this invention is to provide methods of preventing infection in a mammal by administering to the mammal a pharmacologically acceptable and prophylactically effective amount of an analogue of FAA, as defined above. In one embodiment of the invention, the analogue of FAA is administered at dose levels from about 6 mg m$^{-2}$ to about 4,000 mg m$^{-2}$. In another embodiment of the invention, the mammal is infected, or at risk of infection, by a pathogenic organism in the form of a virus, bacteria, fungus or parasite. In yet another embodiment of the invention, the analogue of FAA is DMXAA.

In other aspects, the invention includes methods of treating or preventing infection in a mammal by inducing IRF-3-mediated gene expression via a Toll-like receptor-independent pathway. The induction of IRF-3-mediated gene expression via a Toll-like receptor-independent pathway is achieved by administering to the mammal a pharmacologically acceptable and effective amount of an analogue of FAA, as defined above. In one embodiment, the analogue of FAA is administered at dose levels from about 6 mg m$^{-2}$ to about 4,000 mg m$^{-2}$. In another embodiment, the mammal is infected, or at risk of infection, by a pathogenic organism in the form of a virus, bacteria, fungus or parasite. In yet another embodiment, the analogue of FAA is DMXAA.

Another aspect of the invention relates to a pharmaceutical composition effective for preventing or treating an infection in a mammal comprising an FAA analog as defined above, in combination with one or more pharmaceutically acceptable carriers, diluents or excipients.

In another aspect, an article of manufacture is contemplated in which the agent, as defined above, is packaged for the treatment of a mammal.

In another embodiment of the invention, the agent of the invention is administered or combined with one or more other known or unknown antiviral, antibacterial, antifungal or antiparasitic agents.

The present invention overcomes a major disadvantage of known antimicrobial (anti-viral, anti-bacterial, anti-fungal, and anti-parasitic) agents by providing an effective antiviral agent that is non-toxic to the host. These and other objects are achieved in the present invention.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

FIGS. 3A, 3B and 3C show the effect of DMXAA on the activation of IRF-3 in peritoneal macrophages from C57BL/6 mice that were stimulated with medium alone, LPS (100 ng/ml), or DMXAA (100 µg/ml) for the indicated times (FIG. 3A), peritoneal macrophages from IRF-3$^{+/+}$ and IRF-3$^{-/-}$ mice that were exposed to medium alone or DMXAA (100 µg/ml) for 24 h (FIG. 3B), and TBK1$^{+/+}$ and TBK1$^{-/-}$ mouse embryonic fibroblasts (MEFs) that were stimulated with medium alone, LPS (100 ng/ml), or DMXAA (100 µg/ml) for 2 h (FIG. 3C). Results represent the mean±SE for ≥3 separate experiments.

DESCRIPTION OF THE PREFERRED EMBODIMENTS

Figure 1:
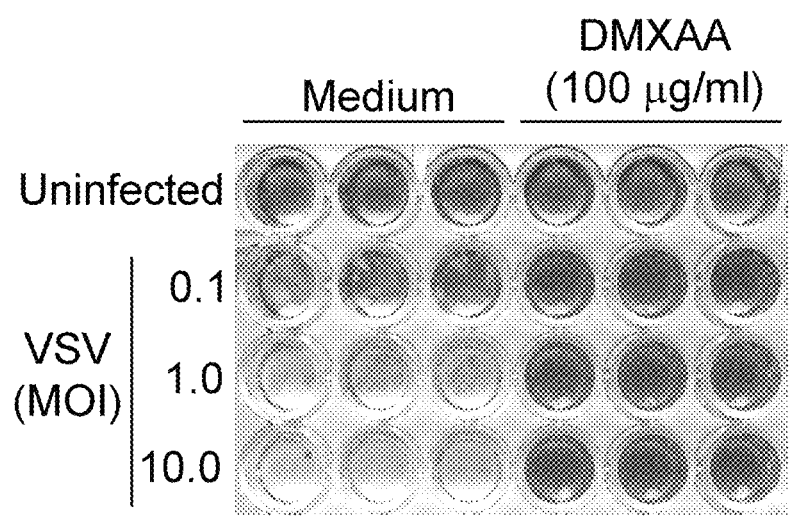
FIG. 1 shows the cytopathic effect of increasing levels of vesicular stomatitis virus (VSV) infection on RAW 264.7 macrophages cultured in medium alone or 100 µg/ml DMXAA (see, Roberts, Z. J. et al. (2007) "*The Chemotherapeutic Agent DMXAA Potently And Specifically Activates The TBK1-IRF-3 Signaling Axis*," J. Exp. Med. 204(7):1559-1569; Vogel, S. N. et al. (1987) "*Macrophages From Endotoxin-Hyporesponsive (Lpsd) C3H/Hej Mice Are Permissive For Vesicular Stomatitis Virus Because Of Reduced Levels Of Endogenous Interferon: Possible Mechanism For Natural Resistance To Virus Infection*," J. Virol. 61(3):812-818).

The present invention relates to the areas of therapeutics, pharmaceuticals, drug discovery, and immunotherapy. More specifically, the present invention relates to methods of stimulating the immune system through the administration of flavone acetic acid [FAA] analogues, and in particular, the flavone acetic acid analogue, 5,6-dimethylxanthenone-4-acetic acid (DMXAA) so as to comprise an antimicrobial therapeutic agent for the treatment of viral, fungal, bacterial or parasitic infections in humans and non-human animals. The invention is especially suitable for use in a process of treating and preventing infection by viruses (for example, rhinoviruses, enteroviruses, and influenza viruses, etc.) and bacteria (especially intracellular bacterial pathogens such as *Francisella tularensis*).

As discussed above, DMXAA causes the ischemic hemorrhagic necrosis of solid tumors in mice, induces the synthesis of tumor necrosis factor alpha (TNF-α), stimulates the production of nitric oxide, activates macrophages to be tumoricidal, and induces cytokines in both human and murine cell lines.

Because all of the cellular activities listed above can be performed by another ubiquitous yet structurally diverse compound, the lipopolysaccharide (LPS) of Gram-negative bacteria, the ability of DMXAA to modulate the expression of a subset of well-characterized LPS-inducible early genes in macrophages was studied in an effort to further elucidate the mechanism of DMXAA action. DMXAA's ability to induce IFN production by macrophages and to modulate the expression of the genes that encode transcription factors IRF-1, IRF-2, and ICSBP members of the interferon regulatory factor (IRF) gene family was also studied.

Six genes are considered to be inducible by lipopolysaccharides ("LPS-inducible") of Gram-negative bacteria, meaning that, in the presence of LPS, transcription of these genes is up-regulated significantly. These genes are: TNF-α, IL-1β, IP-10, Type 2 Tumor Necrosis Factor Receptor (TNFR-2), D3, and D8. In the presence of DMXAA, expression of the genes encoding IP-10, D8, and D3 has been found to be up-regulated to levels similar to those observed upon LPS induction. DMXAA, however, has been found to cause only low induction of TNF-α gene expression and insignificant induction of TNFR-2 and IL-1β genes. DMXAA is an extremely potent inducer of Type 1 Interferons (IFNs) in mouse macrophages, through increased expression of IRF-3 as well as IRF-1, IRF-2 and ICSBP (IRF-8), whereas LPS preferentially stimulates the production of TNF-α, which initiates another aspect of innate immunity, involving the 40- to 45-kDa tyrosine phosphoproteins. These findings suggest that DMXAA activates macrophages by dissectible signaling pathways, and that some of these pathways may overlap with those of bacterial LPS and result in macrophage products that may be central to its role as an antitumor agent.

Despite accumulating evidence of the mechanisms of action of DMXAA and its ability to act as a potent antitumor agent (see, U.S. Pat. Nos. 5,281,620; 6,667,337; 6,495,585; Aitken et al. (1996) "*Synthesis And Antitumor Activity Of New Derivatives Of Flavone-8-Acetic Acid (FAA). Part 1: 6-Methyl Derivatives*," Arch. Pharm. (Weinheim) 329(11): 489-497; Aitken et al. (1997) "*Synthesis And Antitumor Activity Of New Derivatives Of Flavone-8-Acetic Acid (FAA). Part 2: Ring-Substituted Derivatives*," Arch. Pharm. (Weinheim) 330(7):215-224; Aitken et al. (1998) "*Synthesis and antitumor activity of new derivatives of flavone-8-acetic acid (FAA). Part 3: 2-Heteroaryl derivatives*," Arch. Pharm. (Weinheim) 331 (12): 405-411; Aitken et al. (2000) "*Synthesis And Antitumor Activity Of New Derivatives Of Flavone-8-Acetic Acid (FAA). Part 4: Variation Of The Basic Structure*," Arch. Pharm. (Weinheim) 333(6):181-188; Baguley, B. C. (2001) "*Small-Molecule Cytokine Inducers Causing Tumor Necrosis*", Curr. Opin. Investig. Drugs 2(7):967-975; Gobbi et al. (2006) "*New Derivatives Of Xanthenone-4-Acetic Acid: Synthesis, Pharmacological Profile And Effect On TNF-Alpha And NO Production In Human Immune Cells*," Bioorg. Med. Chem. 14(12):4101-4109; Philpott et al. (1997) "*Production Of Tumor Necrosis Factor Alpha By Cultured Human Peripheral Blood Leucocytes In Response To The Anti-Tumor Agent 5,6-Dimethylxanthenone-4-Acetic Acid (NSC 640488)*," Br. J. Cancer 76(12):1586-1591; Zhou et al. (2002) "*5,6-Dimethylxanthenone-4-Acetic Acid (DMXAA): A New Biological Response Modifier For Cancer Therapy*," Invest. New Drugs 20(3):281-295), there is no prior-reported evidence of its ability to act as an immune-stimulating agent for prevention and treatment of microbial, and in particular, viral and bacterial infections. The present invention relates to the ability of FAA analogues (and in particular DMXAA) to stimulate the immune system so as to comprise an antimicrobial therapeutic agent for the treatment of viral, fungal, bacterial or parasitic infections in humans and non-human animals.

As used herein, the term "stimulating the immune system" relates to a process by which the innate immune response is stimulated to respond to the presence of a microbial agent. An example of such stimulation is the induction of interferon regulatory factor-3-mediated gene expression via a Toll-like receptor-independent pathway.

The term "Toll-like receptors" (TLRs) as used herein is intended to refer to a particular receptor family that enables pathogens to be sensed by the host. TLRs are expressed either on the surface or on an endosomal membrane of immune cells where they detect conserved pathogen-associated molecular patterns (PAMP). PAMP-induced oligomerization of TLRs recruits intracellular adapter molecules to the C-terminal domain. Differential engagement of PAMPs through the N-terminus, coupled with differential recruitment and utilization of individual adapter molecules by the different TLRs, provides the basis for the specificity with which cells respond to different PAMPs with different patterns of gene expression (see, for example, Vogel, S. N. et al. (2003) "*TLRs: Differential Adapter Utilization By Toll-Like Receptors Mediates TLR-Specific Patterns Of Gene Expression*," Molecular Intervention 3:466-477).

To date, four adapters, i.e., MyD88, TIRAP, TRAM, and TRIF, have been associated with TLR signaling. MyD88 is absolutely required for the response to PAMPs detected by all known TLRs with the exception of TLR 3 (see, for example, Kawai, T. et al. (1999) "*Unresponsiveness Of MyDd88-Deficient Mice To Endotoxin*," Immunity 11:115-122; Toshchakov, V. et al. (2002) "*TLR4, But Not TLR2, Mediates IFN-Beta-Induced STAT1alpha/Beta-Dependent Gene Expression In Macrophages*," Nature Immunology 3:392-398; Schnare, M. et al. (2000) "*Recognition Of CpG DNA Is Mediated By Signaling Pathways Dependent On The Adaptor Protein MyD88*," Current Biology 10:1139-1142; Hayashi, F. et al. (2001) "*The Innate Immune Response To Bacterial Flagellin Is Mediated By Toll-Like Receptor 5*," Nature 410: 1099-1103; and Hemmi, H. et al. (2002) "*Small Anti-Viral Compounds Activate Immune Cells Via The TLR7MyD88-Dependent Signaling Pathway*," Nature Immunology 3:196-200). In the case of TLR4, all four adapters are utilized and the intracellular signaling cascade bifurcates into "MyD88-dependent" (i.e., MyD88- and TIRAP-mediated) and "MyD88-independent" (i.e., TRAM- and TRIF-mediated) arms (see, for example, Toshchakov, V. et al. (2002) "*TLR4, But Not TLR2, Mediates IFN-Beta-Induced STAT1alpha/Beta-Dependent Gene Expression In Macrophages*," Nature Immunology 3:392-398). MyD88-dependent signaling leads to rapid recruitment of IRAK-family kinases, phosphorylation of IκBα, nuclear translocation of NF-κB, and expression of proinflammatory genes like TNF-α and IL-1β (see, for example, Akira, S. et al. (2006) "*Pathogen Recognition And Innate Immunity*," Cell 124:783-801). In the case of TLR4, the MyD88-independent pathway utilizes TRAM to recruit TRIF that, in turn, recruits two non-cannonical IκB kinases, TANK-Binding Kinase 1 (TBK1) and IκB kinase-ε (IKKε) (see, for example, Yamamoto, M. et al. (2002) "*Cutting Edge: A Novel Toll/IL-1 Receptor Domain-Containing Adapter That Preferentially Activates The IFN-Beta Promoter In The Toll-Like Receptor Signaling*," J. Immunol. 169:6668-6672 and Fitzgerald, K. A. et al. (2003) "*IKKepsilon And TBK1 Are Essential Components Of The IRF3 Signaling Pathway*," Nature Immunol. 4:491-496). Both phosphorylate the transcription factor IFN regulatory factor (IRF)-3 and result in a later wave of NF-κB translocation (see, for example, Covert, M. W. et al. (2005) "*Achieving Stability Of Lipopolysaccharide-Induced NF-kappaB Activation*," Science 309:1854-1857). Once phosphorylated, IRF-3 and NF-κB translocate to the nucleus where they activate genes such as IFN-β.

One skilled in the art will understand that there are TLR-independent pathways leading to IFN-β expression (see, for example, Yoneyama, M. et al. (2004), "*The RNA Helicase RIG-1Has An Essential Function In Double-Stranded RNA-Induced Innate Antiviral Responses*," Nature Immunol. 5:730-737). For example, rather than a TLR, a cytosolic RNA-helicase, retinoic acid-inducible gene-I (RIG-I), detects double-stranded viral RNA via its helicase domain. RIG-I binds to an adapter molecule, MAVS, which leads to TBK1/IKKε activation, IRF-3 phosphorylation, and IFN-β transcription (see, for example, Johnson, C. L. et al. (2006) "*CARD Games Between Virus And Host Get A New Player*," Trends Immunol. 27:1-4). Another RIG-1-like molecule, Melanoma-differentiation associated gene-5 (Mda-5), has also been described (see, for example, Kang, D. C. et al. (2002) "mda-5: *An Interferon-Inducible Putative RNA Helicase With Double-Stranded RNA-Dependent Atpase Activity And Melanoma Growth-Suppressive Properties*," Proc. Natl. Acad. Sci. (U.S.A.) 99:637-642). RIG-I and Mda-5 distinguish between different RNA viruses (see, for example, Kato, H. et al. (2006) "*Differential Roles Of MDA5 and RIG-1Helicases In The Recognition Of RNA Viruses*," Nature 441:101-105). Another pathway leading to IRF-3 activation has also been described recently (see, for example, Stetson, D. B. et al. (2006) "*Recognition Of Cytosolic DNA Activates An IRF3-Dependent Innate Immune Response*," Immunity 24:93-103). Although the molecular sensor was not identified, cytosolic DNA has been found to activate IRF-3 and induce IFN-β in the absence of detectable NF-κB or MAPK activation.

As used herein, the term "flavone acetic acid [FAA] analogues" refers to compounds having the formula (I):

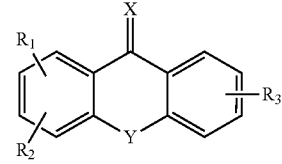

Formula (I)

wherein:

X and Y are O or N, and $R_1$, $R_2$, and $R_3$ are each independently chosen from H, $C_1$-$C_6$ alkyl, halogen, $CF_3$, CN, $NO_2$, $NH_2$, OH, OR, NHCOR, $NHSO_2R$, SR, $SO_2R$, $CH_2COOH$, or NHR, wherein each R is independently $C_1$-$C_6$ alkyl optionally substituted with one or more substituents selected from hydroxy, amino, ethoxy, or methoxy, and each of $R_1$, $R_2$, and $R_3$ may be present at any one of the available carbon positions 1 to 8;

in each of the carbocyclic aromatic rings in formula (I), up to two of the methane (—CH=) groups may be replaced by an aza (—N=) group; and any two of $R_1$, $R_2$, and $R_3$ may additionally together represent the group —CH=CH—CH=CH—, such that this group, together with the carbon or nitrogen atoms to which it is attached, forms a fused six membered aromatic ring, or a pharmaceutically acceptable salt or ester thereof (see, e.g., Remington's Pharmaceutical Sciences, 19th Edition, A. R. Gennaro, ed., Mack Publishing Co., Easton, Pa. (1995), incorporated herein by reference in its entirety).

An analogue of FAA, according to the present invention, is understood to be a chemical compound with a structure similar to that of flavone acetic acid but differing from it with respect to certain biological properties. The analogue of FAA of the invention may have other similar or dissimilar functions, metabolisms, mechanisms of action, or other biochemical, physiological, or pharmacological actions when compared with FAA.

The invention particularly concerns the FAA analogue: DMXAA (5,6-dimethylxanthenone-4-acetic acid):

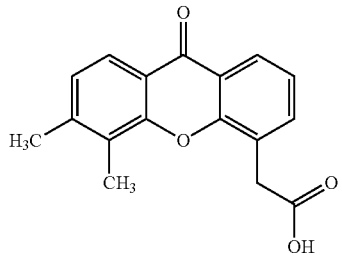

As used herein, the term "microbial" is intended to denote bacterial, viral, fungal or parasitic pathogens.

Pathogenic bacteria are bacteria that are capable of causing either intracellular or extracellular infections in humans and animals. Examples of pathogenic bacteria that may be treated in accordance with the present invention include: *Bordetella* spp., *Borrelia* spp., *Brucella* spp., *Campylobacter* spp., *Clostridia* spp. (e.g., *C. botulinum*), *Corynebacterium* spp., *Enterobacter* spp., *Escherichia coli* spp., *Francisella* spp. (e.g., *F. tularensis*, etc.); *Haemophilus* spp. (e.g., *H. influenzae*, *H. hemolyticus*, etc.); *Helicobacter* spp. (e.g., *H. pylori*); *Listeria* spp. (e.g., *L. monocytogenes*); *Mycobacterium* spp. (e.g., *M. tuberculosis*); *Neisseria* spp. (e.g., *N. gonorrheae*, *N. meningitidis*, etc.); *Pseudomonas* spp. (e.g., *P. aeruginosa*); *Salmonella* spp. (e.g., *S. typhi*, etc.); *Shigella* spp.; *Staphylococcus* spp. (e.g., *S. aureus*, etc.); *Streptococcus* spp. (e.g., *S. pneumoniae*, *S. pyogenes*, etc.); *Treponema* spp. (e.g., *T. pallidum*); *Vibrio* spp. (e.g., *V. cholera*); *Yersinia* spp. (e.g., *Y. pestis*, etc.), etc.

Pathogenic viruses are infectious agents that lack capacity for independent metabolism and, thus, must replicate within living host cells. Examples of pathogenic viruses that may be treated in accordance with the present invention include: DNA viruses (such as herpes simplex viruses, varicella-zoster virus, Epstein-Barr virus, cytomegalovirus, human herpesvirus (types 6, 7, and 8), smallpox, vaccinia and other poxviruses, parvovirus, and human papillomaviruses) and RNA viruses (such as human retroviruses (e.g., HIV, HTLV, etc.), influenza viruses, rotaviruses, enteroviruses and reoviruses, rubeola, rubella, mumps, rabies and other rhabdoviruses, arthropod- and rodent-borne viruses, and Marburg and Ebola viruses. The invention particularly concerns and is illustrated below with respect to "respiratory" viruses (either DNA or RNA viruses) such as rhinoviruses, coronaviruses, respiratory syncytial virus, parainfluenza viruses, adenoviruses, influenza A and B viruses, enteroviruses, and herpes simplex viruses. Enteroviruses are RNA viruses of the Picornaviridae family, including for example polioviruses and non-polioviruses. Non-polioviruses include for example, Coxsackie A viruses, Coxsackie B viruses, echoviruses, and other enteroviruses.

Examples of pathogenic fungi that may be treated in accordance with the present invention include: *Ajellomyces* spp. (e.g., *A. capsulatus*, *A. dermatitidis*, etc.), *Arthroderma* spp. (e.g., *A. benhamiae*, *A. gypseum*, etc.), *Aspergillus* spp. (e.g., *A. flavus*, *A. fumigatus*, *A. niger*, etc.) *Absidia corymbifera*, *Blastomyces dermatitidis*, *Candida* spp. (e.g., *C. albicans*, *C. dublinensis*, *C. glabrata*, *C. parapsilosis*, etc.), *Coccidioides immitis*, *Cryptococcus neoformans*, *Epidermophyton floccosum*, *Histoplasma capsulatum*, *Malassezia* spp. (e.g., *M. furfur*, *M. globosa*, etc.), *Microsporum* spp. (e.g., *M. canis*, *M. fulvum*, *M. gypseum*, etc.), *Paracoccidioides brasiliensis*, *Penicillium marneffei*, *Pichia anomala*, *Pneumocystis jirovecii*, *Rhizopus oryzae*, *Schizophyllum commune*, *Trichophyton* spp. (e.g., *T. mentagrophytes*, *T. rubrum*, *T. tonsurans*, etc.), *Trichosporon* spp. (e.g., *T. asahii*, *T cutaneum*, *T. inkin*, etc.).

Examples of pathogenic parasites that may be treated in accordance with the present invention include: *Ascaris lumbricoides*, *Acarapis woodi*, *Acanthocephala*, *Balantinium coli*, *Clonorchis sinensis*, *Cryptosporidium parvum*, *Cyclospora cayatanensis*, *Diphyllobothrium latum*, *Encephalitozzon* spp. (e.g., *E. hellem*, *E. cuniculi*), *Entamoeba histolytica*, *Enterobius vermicularis*, *Enterocytozoon bieneusi*, *Fasciola hepatica*, *Giardia lamblia*, *Naegleria fowleri*, *Plasmodium falciparum*, *Pyrenophora teres*, *Trichuris trichiuria*, *Trichomonas vaginalis*, *Strongyloides stercoralis*, *Trypanosoma brucei*, *Taenia* spp. (e.g., *T. solium*, *T. saginata*), *Toxocara canis*, *Toxoplasma gondii*, *Trichinella spiralis*, *Trypanosoma* spp. (e.g., *T. cruzi*, *T. vivax*, etc.), *Leishmania* spp. (e.g., *L. donovani*, *L. infantum*, *L. chagasi*, *L. mexicana*, *L. amazonensis*, *L. venezuelensis*; *L. tropica*; *L. major*; *L. aethiopica*; and the subgenus *Viannia* with four main species (*L.* (*V.*) *braziliensis*, *L.* (*V.*) *guyanensis*, *L.* (*V.*) *panamensis*, and *L.* (*V.*) *peruviana*), etc.).

The compositions and methods of the present invention are intended for the treatment of infection in humans and non-human animals (especially mammals, such as cattle, dogs, swine, cats, horses, etc.).

The compositions of the present invention may advantageously be provided alone or in concert with other antimicrobial agents, such as antibacterial agents (e.g., amikacin, amoxicillin, ampicillin, azithromycin, azlocillin, aztreonam, aztreonam, bacitracin, carbacephem, carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, cephalexin, ciprofloxacin, clarithromycin, cloxacillin, colistin, demeclocycline, dicloxacillin, dirithromycin, doripenem, doxycycline, enoxacin, ertapenem, erythromycin, flucloxacillin, gatifloxacin, geldanamycin, gentamicin, herbimycin, imipenem/cilastatin, kanamycin, levofloxacin, lomefloxacin, loracarbef, mafenide, meropenem, mezlocillin, minocycline, moxifloxacin, nafcillin, neomycin, netilmicin, norfloxacin, ofloxacin, oxytetracycline, paromomycin, penicillin, piperacillin, polymyxinB, prontosil, roxithromycin, streptomycin, sulfacetamide, sulfamethizole, sulfanilimide, sulfasalazine, sulfisoxazole, teicoplanin, telithromycin, tetracycline, ticarcillin, tobramycin, trimethoprim, trimethoprim-sulfamethoxazole, troleandomycin, trovafloxacin, vancomycin, etc.), antiviral agents (e.g., abacavir, acyclovir, amantadine, didanosine, emtricitabine, enfuvirtide, entecavir, ganciclovir, gardasil, lamivudine, nevirapine, nelfinavir, oseltamivir, ribavirin, rimantadine, ritonavir, stavudine, valaciclovir, vidarabine, zalcitabine, and zidovudine, etc.), antifungal agents (e.g., amorolfine, amphotericin, anidulafungin bifonazole butenafine, butoconazole, caspofungin ciclopirox olamine clioquinol, clotrimazole, econazole, fenticonazole fezatione, fluconazole flucytosine, griseofulvin, isavuconazole isoconazole, itraconazole, ketoconazole lanoconazole, micafungin miconazole, naftifine neticonazole, nystatin, oxiconazole posaconazole ravuconazole salicylic acid, sertaconazole sodium pyrithione. terbinafine, terconazole, ticlatone, tioconazole, tolnaftate, triacetin, voriconazole, zinc pyrithione, etc.), or antiparasitic agents (e.g., amphotericin, antimony, chloroquine, diethycarbazine, iodoquinol, mebendazole, meglumine antimoniate, melarsoprol, metronidazole, miltefosine, niclosamide, paromomycin, pentamidine, piperazine, praziquantel, pyrantel, quinacrine, rifampin, sodium stibogluconate, suramin, tetracycline, thiabendazole, etc.).

One skilled in the art would also understand that other agents with antimicrobial activity may not yet have been discovered and that the compositions of the present invention may be combined with any other agent that is found to contain the ability to suppress or inhibit circulating pathogen as evidenced by reduced presence of anti-pathogen antibodies, reduced presence of culturable pathogen, and/or reduced presence of antigen in the recipient's serum.

Any suitable route of administration may be employed for providing a mammal with an effective dosage of an analogue of FAA according to the present invention. A suitable route of administration may be determined readily by one skilled in the art of pharmacology without undue experimentation. For example, the dosage may be administered orally, parenterally, topically, intraarterially, introperitoneally, intraveneously, intranasally, intrapleurally, intraoccularly, by injection, subcutaneously, or the like. It is understood that injection comprises also perfusion and continuous infusion. Dosage forms include tablets, capsules, powders, solutions, dispersions, suspensions, ointments, and aerosols.

It is understood that the analogue of FAA is to be administered in pharmacologically or physiologically acceptable amounts, by which is to be understood amounts not harmful to the patient, or amounts where any harmful side effects in individual patients are outweighed by the benefits. Similarly, the analogue of FAA is to be administered in a therapeutically effective amount, which is to be understood as an amount meeting the intended therapeutic objectives, and providing the benefits available from administration of an anti-pathogen agent.

In one object of the invention, an analogue of FAA will be administered prophylactically, in dosages substantially similar to those for treatment, to mammals that are deemed to be at risk of infection or have already been exposed to a pathogen. It is anticipated that any mammal and, especially, young children, immunocompromised individuals, travelers, military personnel, healthcare workers, and the elderly, among others, would be candidates for prophylactic treatment with analogues of FAA.

The dosage ranges for administration of analogues of FAA are those which produce the desired effect whereby symptoms of infection are ameliorated or prevented. For example, an effective amount for therapy of influenza virus infection refers to the amount administered to maintain an amount that suppresses or inhibits circulating virus throughout the period during which infection is evidenced such as by the presence of antiviral antibodies, presence of culturable virus, and presence of viral antigen in patient serum. The dosage will vary generally with the age, weight, and response of the individual patient. The dosage will also vary with the nature or the severity of the pathogen and infection, with the particular analogue of FAA, with the concomitant use of other active compounds, and the route of administration. In addition, the dosage will be determined by the existence of any adverse side effects such as immune tolerance.

An effective dose of an analogue of FAA can be determined without undue experimentation (for example, by pharmacokinetic studies) by one skilled in the art after consideration of all the criteria and use of best judgment on the patient's behalf. In one embodiment, an analogue of FAA is administered at dose levels from about 6 mg m$^{-2}$ to about 4,000 mg m$^{-2}$. It is anticipated that an analogue of FAA, such as DMXAA, may be administered in appropriate doses (see, e.g., Jameson, M. B. et al. (2007) "*Pharmacokinetics Of 5,6-Dimethylxanthenone-4-Acetic Acid (AS1404), A Novel Vascular Disrupting Agent, In Phase I Clinical Trial*," Canc. Chemother. Pharmacol. 59(5):681-687; McKeage, M. J. et al. (2006) "*5,6-Dimethylxanthenone-4-Acetic Acid In The Treatment Of Refractory Tumors: A Phase I Safety Study Of A Vascular Disrupting Agent*," Clin. Canc. Res. 12(6):1776-1784; Zhao, L. et al. (2003) "*Improvement Of The Antitumor Activity Of Intraperitoneally And Orally Administered 5,6-Dimethylxanthenone-4-Acetic Acid By Optimal Scheduling*," Clin. Canc. Res. 9(17):6545-6550; Rustin, G. J. et al. (2003) "*5,6-Dimethylxanthenone-4-Acetic Acid (DMXAA), A Novel Antivascular Agent: Phase I Clinical And Pharmacokinetic Study*," Br. J. Canc. 88(8):1160-1167), and in one or multiple courses of treatment or until infection is resolved or excessive toxicity is observed.

One object of the present invention is to provide a method of treating a microbial pathogen infection in a mammal by administering to the mammal a pharmacologically acceptable and therapeutically effective amount of an analogue of FAA, as defined above. Having now generally described the invention, the same will be more readily understood through reference to the following examples, which are provided by way of illustration and are not intended to be limiting of the present invention unless specified.

EXAMPLE 1

Materials and Methods

Methods employed are as described by Roberts, Z. J. et al. (2007) ("*The Chemotherapeutic Agent DMXAA Potently And Specifically Activates The TBK1-IRF-3 Signaling Axis*," J. Exp. Med. 204(7):1559-1569), and Vogel, S. N. et al. (1987) ("*Macrophages From Endotoxin-Hyporesponsive (Lpsd) C3H/Hej Mice Are Permissive For Vesicular Stomatitis Virus Because Of Reduced Levels Of Endogenous Interferon: Possible Mechanism For Natural Resistance To Virus Infection*," J. Virol. 61(3):812-818), except as indicated below.

Cells and Cell Culture

Thioglycollate-elicited murine peritoneal macrophages were obtained from 5- to 6-wk-old female C57BL/6J mice (The Jackson Laboratory, Bar Harbor, Me.), IRF-3$^{+/+}$ and IRF-3$^{-/-}$ mice (Dr. Tadatsugu Taniguchi, University of Tokyo, Tokyo, Japan) and TLR4$^{+/+}$ and TRL4$^{-/-}$ mice. Murine macrophage-like RAW 264.7 cells and Madin-Darby canine kidney (MDCK) cells were obtained from the American Type Culture Collection (Manassas, Va.). MEFs from TBK1$^{+/+}$ and TBK1$^{-/-}$ mice from Dr. Wen-Chen Yeh (University of Toronto, Toronto, Canada).

Thioglycollate-elicited murine peritoneal macrophages were cultured as described in Medvedev, A. E. et al. (2000) "*Inhibition Of Lipopolysaccharide-Induced Signal Transduction In Endotoxin-Tolerized Mouse Macrophages: Dysregulation Of Cytokine, Chemokine, And Toll-Like Receptor 2 And 4 Gene Expression*," J. Immunol. 164:5564-5574. MEFs and RAW 264.7 macrophages were cultured in DMEM (Bio-Whittaker, Walkersville, Md.), supplemented with 10% (v/v) FBS (HyClone Laboratories, Logan, Utah), 10,000 U/ml penicillin, and 10,000 µg/ml streptomycin at 37° C. in 5% $CO_2$ in air. The endotoxin content in the medium was <0.01 EU/ml, according to the manufacturer's specifications. Only cells passaged ≤20 times were used.

Reagents

DMXAA (sodium salt; MW 304) was synthesized at the Auckland Cancer Society Research Centre (Rewcastle, G. W. et al. (1989) "*Potential Antitumor Agents, 58, Synthesis And Structure-Activity Relationships Of Substituted Xanthenone-*

4-*Acetic Acids Active Against The Colon* 38 *Tumor In Vivo*," J. Med. Chem. 32:793-799). Protein-free *Escherichia coli* K235 LPS (McIntire, F. C. et al. (1969) "*Studies On A Lipopolysaccharide From Escherichia coli. Heterogeneity And Mechanism Of Reversible Inactivation By Sodium Deoxycholate*," Biochemistry 10:4063-4067) was used as a TLR4 agonist. Poly I:C (Amersham Biosciences, Piscataway, N.J.) was used as a TLR3 agonist. Purified IRF-3 (aa 173-427) was from Dr. Kai Lin (University of Massachusetts Medical School, Worcester, Mass.). Vesicular stomatitis virus (VSV), strain Indiana, was obtained from the American Type Culture Collection (Manassas, Va.).

VSV Infection of Macrophages

RAW 264.7 macrophages were seeded at $5 \times 10^4$ cells/well in 96-well plates and allowed to incubate overnight (see, generally, Falk, L. A. et al. (1990) "*Differential Production Of IFN-Alpha/Beta By CSF-1-And GM-CSF-Derived Macrophages*," J. Leukoc. Biol. 48(1):43-49). The following day, cells were either pretreated with complete DMEM alone or complete DMEM supplemented DMXAA for 6 h. Cells were then infected with VSV at various multiplicities of infection (MOI) in serum-free medium for 1 h. After the infection, the serum-free medium was replaced with complete DMEM alone or complete DMEM supplemented with DMXAA. After 19 h, the medium was removed and the cells were fixed in 4% formalin and stained with crystal violet. The absence of crystal violet stained cells is indicative of the cytopathic effect (CPE) of viral infection.

Influenza Virus Infection of MDCK Cells

Assay of Direct Inhibition of Viral Infection

Various concentrations of DMXAA were aliquoted in 50 µl volumes to quadruplicate wells of 96-well plates. Influenza at $10^3$ $TCID_{50}$ was added in 50 µl volumes to all wells and incubated at room temperature for 1 h. The mixture was inoculated onto MDCK cells on 96-well plates. Tamiflu (1.75 mg/ml) and Relenza (0.5 mg/ml) were used as a positive control for the assay. Plates were incubated for 4 days and stained with crystal violet to determine CPE.

Assay of Indirect Inhibition of Viral Infection

Various concentrations of DMXAA were aliquoted in 50 µl volumes onto MDCK cells in quadruplicate wells of 96-well plates. After 1 h incubation at 37° C., Influenza/A/Wuhan at $10^3$ $TCID_{50}$ was inoculated onto the plates. Plates were incubated for 4 days and stained with crystal violet to determine CPE.

Quantitative Real-Time PCR

Primers for detection of IFN-β, RANTES, TNF-α, and hypoxanthine phosphoribosyltransferase (HPRT) mRNAs were designed using the Primer Express 2.0 program (Applied Biosystems). Total cDNA (31.25 ng) was used as starting material for real-time PCR quantitation with SYBR® Green (Applied Biosystems, Foster City, Calif.) on an Applied Biosystems 7900HT. Ct values were compared using the DD-Ct method using HPRT as a housekeeping gene (see, for example, Livak, K. J. et al. (2001) "*Analysis Of Relative Gene Expression Data Using Real-Time Quantitative PCR And The 2(-Delta Delta C(T)) Method*," Methods 25:402-408).

Cytokine Analysis

IFN-β protein in cell culture supernatants was measured using a custom ELISA originally described in Weinstein, S. L. et al. (2000) "*Phosphatidylinositol 3-Kinase And mTOR Mediate Lipopolysaccharide-Stimulated Nitric Oxide Production In Macrophages Via Interferon-Beta*," J. Leukocyte Biol. 67:405-414, with few modifications. Briefly, NUNC Maxisorp 96-well polystyrene plates (NUNC International, Rochester, N.Y.) were coated overnight with a 1:4000 dilution of rat anti-mouse IFN-β mAb (Yamasa, Tokyo, Japan) in 0.1M sodium carbonate at 4° C. Plates were blocked with 10% FCS in 1×PBS for 2 h at room temperature. Samples and a murine IFN-β standard (NIH, Bethesda, Md.) were added to wells and incubated overnight at 4° C. Plates were washed 3× with 1% FCS/PBS-T, followed by incubation with a 1:2000 dilution of rabbit anti-mouse IFN-β pAb (PBL Biomedical Laboratories, Piscataway, N.J.) in 10% FCS-PBS overnight at 4° C. Wells were washed 3× followed by incubation with a 1:2000 dilution of goat anti-rabbit HRP (Cell Signaling Technologies, Beverly, Mass.) in 10% FCS-PBS for 1 h at room temperature. Plates were washed 3× and developed with TMB substrate (KPL, Gaithersburg, Md.). The reaction was stopped by addition of 1N $H_2SO_4$, and plates were read at 450 nm. RANTES and TNF-α were quantified using Luminex bead-based colorimetric assays.

Antibodies and Native-PAGE

Rabbit anti-mouse IκBα phospho-specific Ab (pAb) was purchased from Santa Cruz Biotechnology, Inc. (Santa Cruz, Calif.). Rabbit anti-mouse MAPK pAb and rabbit anti-human phospho-IRF-3 pAb antibodies were purchased from Cell Signaling (Danvers, Mass.). Rabbit anti-mouse IRF-3 pAb was purchased from Zymed (South San Francisco, Calif.). Native-PAGE for the detection of IRF-3 dimers was carried out as described in Iwamura, T. et al. (2001) "*Induction Of IRF-3/-7 Kinase And NF-kappaB in Response To Double-Stranded RNA And Virus Infection: Common And Unique Pathways*," Genes and Cells 6:375-388. Briefly, thioglycolate-elicited peritoneal macrophages were lysed following stimulation with either LPS or DMXAA as indicated. Proteins were separated in the absence of SDS in 7.5% Tris-Glycine gels (Bio-Rad, Hercules, Calif.) and transferred to PVDF. Membranes were probed with a 1:250 dilution of rabbit anti-mouse IRF-3 for 1 h at room temperature. Goat anti-rabbit IgG-HRP (Cell Signaling Technologies, Danvers, Mass.) at a 1:2000 dilution was used as the secondary Ab. Blots were developed with ECL Plus (Amersham Biosciences, Piscataway, N.J.).

Rantes Elisa

MEFs were prepared from day 13.5 to 14.5 embryos of $MAVS^{+/+}$ and $MAVS^{-/-}$ mice. MEFs were treated with medium alone, DMXAA (100 µg/ml), LPS (100 µg/ml), or poly (I:C) (10 µg/ml) for 24 h. For stimulation of cells, poly (I:C) was mixed with Fugene 6 transfection reagent (Roche) at a ratio of 1:1 (volume:weight) in OptiMEM medium and incubated for 15 min prior to stimulation. Culture supernatants of cells ($2 \times 10^4$) seeded on 96-well plates were collected after 24 h stimulation and analyzed for RANTES levels with ELISA. ELISA was performed according to the manufacturer's instructions (R&D Systems).

Online Supplemental Material

Microarray analysis was carried out using Affymetrix® mouse array 430A_2 exposed to total RNA prepared from C57BL/6J or IFN-$β^{-/-}$ macrophages that had been treated with medium alone or DMXAA for 3 h. Fold-induction was calculated using Affymetrix® GeneChip® Operating Software. A ≥3-fold increase or decrease between inducible and basal mRNA levels was set as the criteria for inclusion of a gene as modulated.

EXAMPLE 2

Antiviral Activity of DMXAA

FIG. 1 shows that exposure of untreated RAW 264.7 macrophages to increasing titers of VSV results in increasing levels of viral infection and, consequently, increasing CPE (i.e., lysis of macrophages as evidenced by decreasing staining with crystal violet). In contrast, pretreatment of the macrophages for 6 h with 100 µg/ml of DMXAA completely prevents VSV infection and CPE at even the highest level of exposure to VSV (i.e., MOI=10.0).

TABLE 1 demonstrates that DMXAA inhibits the CPE of influenza virus on MDCK cells. The $IC_{50}$s for DMXAA's direct and indirect antiviral activities are 5.0 µg/ml and 2.0 µg/ml, respectively.

TABLE 1

Inhibition Assay for DMXAA Against Influenza/A/Wuhan

| [ ] Test Compound per ml | Direct (CPE) | Indirect (CPE) |
|---|---|---|
| 100 ug DMXAA | ++++ | ++++ |
| 25 ug DMXAA | ++++ | ++++ |
| 6.25 ug DMXAA | ++++ | ++++ |
| 1.56 ug DMXAA | +-+- | +++- |
| .39 ug DMXAA | ---- | --+- |
| .01 ug DMXAA | ---- | ---- |
| .024 ug DMXAA | ---- | ---- |
| .0006 ug DMXAA | ---- | ---- |
| Tamiflu (0.1 ug) | -+++ | |
| Relenza (0.12 ug) | -+++ | |
| Virus Control | ---- | |

EXAMPLE 3

DMXAA Activation of IRF-3-Mediated Gene Expression

Figure 2A:
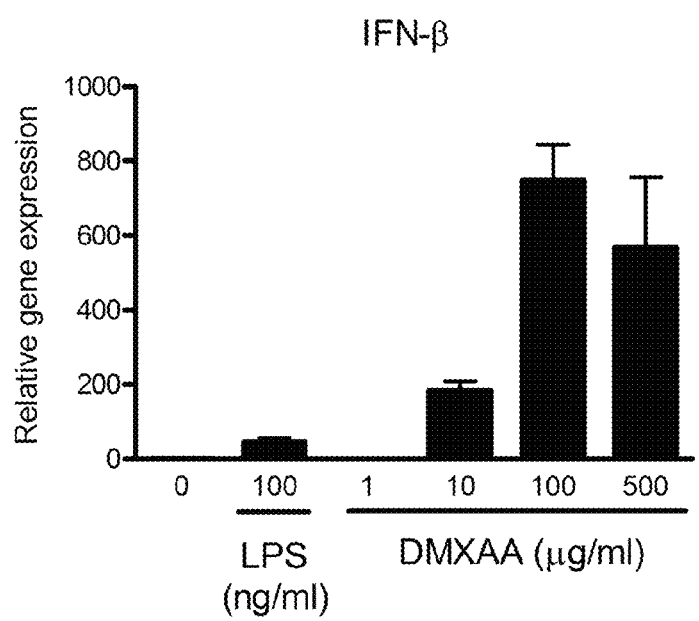
FIGS. 2A, 2B, 2C, 2D and 2E show the effects of DMXAA on IRF-3-mediated gene expression in peritoneal macrophages from C57BL/6 mice that were stimulated for 2 h with LPS (100 ng/ml) or increasing concentrations of DMXAA (FIG. 2A), primary murine macrophages that were stimulated with medium alone, LPS (100 ng/ml), or DMXAA (100 µg/ml) for the indicated times (FIG. 2B), RAW 264.7 macrophages that were stimulated with medium alone, LPS (10 ng/ml), or DMXAA (1 mg/ml) for the indicated times (FIG. 2C), peritoneal macrophages from C57BL/6 mice that were stimulated with medium alone, LPS (100 ng/ml), or DMXAA (100 µg/ml) for the indicated times (FIG. 2D), and peritoneal macrophages from TLR4$^{+/+}$ and TLR4$^{-/-}$ mice that were stimulated with medium alone, LPS (100 ng/ml), or DMXAA (100 µg/ml) for 2 h (FIG. 2E). Results represent the mean±SE for ≥3 separate experiments.
Figure 2B:
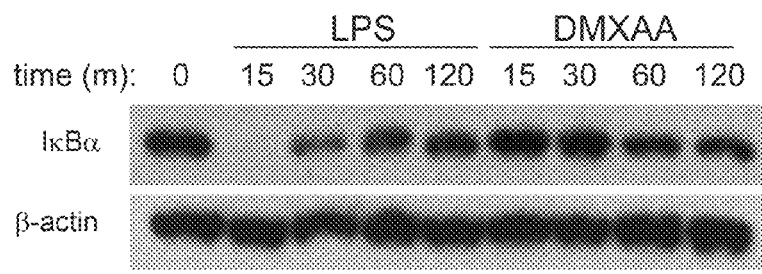
Figure 2C:
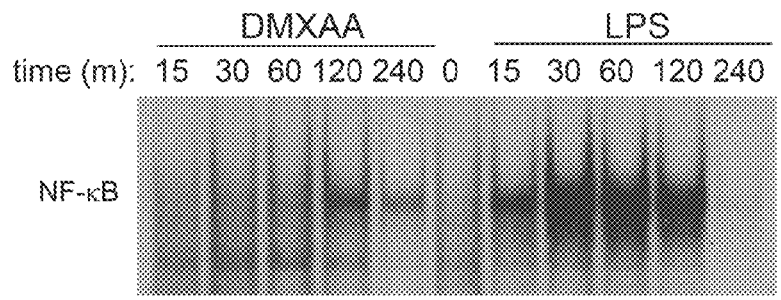
Figure 2D:
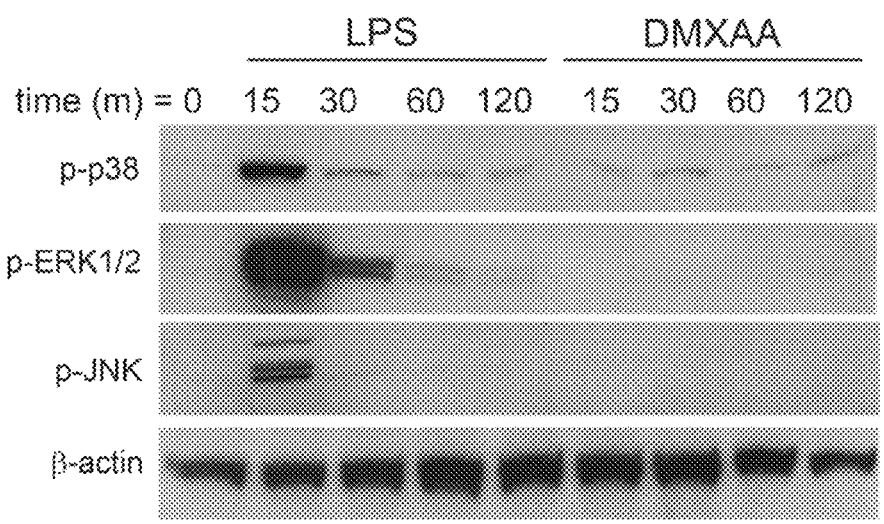
Figure 2E:
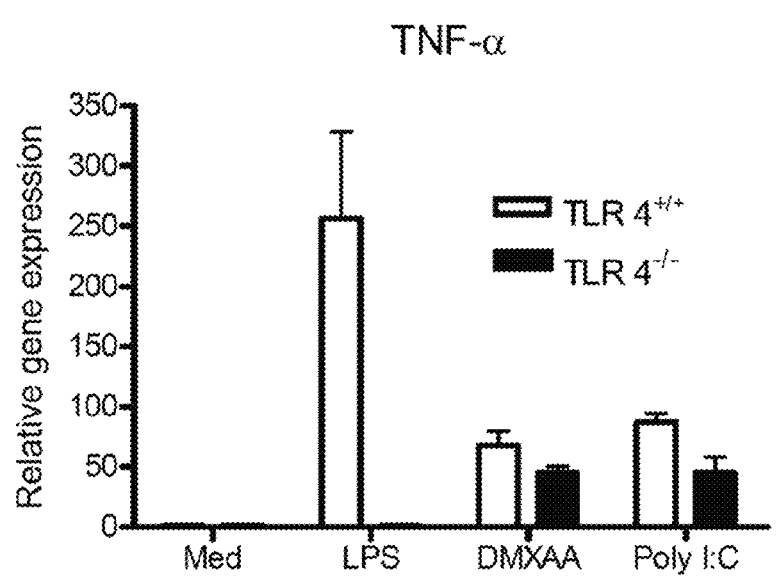

FIGS. 2A, 2B, 2C, 2D and 2E demonstrate that DMXAA is a much more potent inducer of IFN-β protein and IP-10 mRNA in murine macrophages than LPS, while LPS stimulation results in much higher levels of proinflammatory cytokines, e.g., TNF-α and IL-1β. FIG. 2A shows, using real-time PCR to quantify mRNA expression in peritoneal exudate macrophages, that DMXAA induces ~10-fold more IFN-β steady-state mRNA than LPS. While LPS stimulation leads to the rapid disappearance of IκBα (FIG. 2B) and NF-κB translocation (FIG. 2C) in primary macrophages and the RAW 264.7 macrophage-like cell line, respectively, treatment with DMXAA at doses 10-fold above those observed to be saturating in FIG. 2A has little effect on either the level of IκBα protein or NF-κB binding activity. Under conditions where LPS activates p38, ERK, and JNK MAPK in C57BL/6 macrophages, DMXAA has no discernible effect (FIG. 2D). FIG. 2E shows that LPS fails to induce TNF-α mRNA in the absence of TLR4, while both DMXAA and the TLR3-dependent agonist, poly I:C, induces TNF-α to wild-type levels. Collectively, the observations described above support that DMXAA stimulates a pathway that depends primarily on IRF-3, rather than NF-κB, and that DMXAA's activity is both MAPK- and TLR4-independent.

To extend the findings described above at the level of gene expression, C57BL/6 macrophages were stimulated with medium only or DMXAA for 3 h and mRNA were subjected to Affymetrix® microarray analysis. Of ~14,000 genes analyzed, DMXAA results in a ≥3-fold change in expression of 136 genes (110 and 26 genes are up-regulated or down-regulated, respectively) compared to the response of medium-treated cells (Table 2). Because many of the genes that were significantly modulated by DMXAA, such as Mx1, are known to be IFN-β-dependent, the inventors also carried out the same analysis in IFN-β$^{-/-}$ macrophages. A comparison of the results from these two strains reveals that 77 of the 136 genes modulated by DMXAA in wild-type macrophages are IFN-β-dependent (see WT/KO column in Table 2) based on a 3-fold difference. Because TRIF is an adapter required for IRF-3 activation following LPS stimulation (see, for example, Yamamoto, M. et al. (2003) "*Role Of Adaptor TRIF In The MyD88-Independent Toll-Like Receptor Signaling Pathway*," Science 301:640-643), genes identified as poorly LPS-inducible in TRIF$^{-/-}$ macrophages represent a reliable surrogate for IRF-3-dependent gene induction. Many of the same genes induced by DMXAA in the inventors' microarray analysis were identified as being poorly inducible by LPS in macrophages derived from TRIF-null mice (see, for example, Hirotani, T. et al. (2005) "*Regulation Of Lipopolysaccharide-Inducible Genes By MyD88 And Toll/IL-1 Domain Containing Adaptor Inducing IFN-Beta*," Biochem. Biophys. Res. Commun. 328:383-392), e.g., Rantes (Ccl5), Ifit1, Ccl4, and OasI were shown to be highly TRIF-dependent in LPS-treated macrophages. Thus, these data indicate that DMXAA preferentially induces IRF-3-dependent genes (see, Roberts, Z. J. et al. (2007) "*The Chemotherapeutic Agent DMXAA Potently And Specifically Activates The TBK1-IRF-3 Signaling Axis*," J. Exp. Med. 204(7):1559-1569).

TABLE 2

Genes Up- or Down-Regulated ≥3-Fold Following Treatment of Murine Macrophages with DMXAA[a]

| Gene Symbol | GenBank Accession Number | Description | Fold Change: BL/6[b] | Fold Change: IFNβ$^{-/-c}$ | WT/KO[d] |
|---|---|---|---|---|---|
| IL6 | NM_031168 | interleukin 6 (interferon, beta 2) | 564.6 | 13.5 | 41.8 |
| IFNB1 | NM_010510 | interferon, beta 1, fibroblast | 194.1 | 1.1 | 178.6 |
| MX1 | BC007127 | myxovirus (influenza virus) resistance 1, interferon-inducible protein p78 (mouse) | 191.4 | 9.3 | 20.7 |
| CCL2 | U50712 | chemokine (C-C motif) ligand 2 | 125.6 | 5.8 | 21.7 |
| LHX2 | NM_010710 | LIM homeobox 2 | 92.1 | 7.8 | 11.9 |
| TNFRSF11B | AB013898 | tumor necrosis factor receptor superfamily, member 11b (osteoprotegerin) | 90.5 | 100.0 | 0.9 |
| MX2 | M21039 | myxovirus (influenza virus) resistance 2 (mouse) | 85.3 | 1.1 | 74.3 |
| IFNA6 | NM_010504 | interferon, alpha 6 | 77.7 | 9.1 | 8.6 |
| CXCL10 | NM_021274 | chemokine (C-X-C motif) ligand 10 | 69.1 | 21.2 | 3.3 |
| TGTP | NM_011579 | T-cell specific GTPase | 60.2 | 1.6 | 38.6 |
| LOC129607 | NM_020557 | hypothetical protein LOC129607 | 58.9 | 7.8 | 7.6 |
| SOCS1 | AB000710 | suppressor of cytokine signaling 1 | 57.5 | 3.4 | 16.7 |

TABLE 2-continued

Genes Up- or Down-Regulated ≥3-Fold Following
Treatment of Murine Macrophages with DMXAA[a]

| Gene Symbol | GenBank Accession Number | Description | Fold Change: BL/6[b] | Fold Change: IFNβ[−/−c] | WT/ KO[d] |
|---|---|---|---|---|---|
| IFNG | K00083 | interferon, gamma | 46.5 | 59.4 | 0.8 |
| OASL | AB067533 | 2'-5'-oligoadenylate synthetase-like | 35.6 | 19.7 | 1.8 |
| IFIT1 | NM_008331 | interferon-induced protein with tetratricopeptide repeats 1 | 33.5 | 22.2 | 1.5 |
| IFNA5 | NM_010505 | interferon, alpha 5 | 32.4 | 2.5 | 12.9 |
| IFIT3 | NM_010501 | interferon-induced protein with tetratricopeptide repeats 3 | 32.2 | 10.5 | 3.1 |
| IFIT2 | NM_008332 | interferon-induced protein with tetratricopeptide repeats 2 | 27.1 | 14.3 | 1.9 |
| PGF | NM_008827 | placental growth factor, vascular endothelial growth factor-related protein | 25.3 | 20.2 | 1.3 |
| IIGP1 | BM239828 | interferon inducible GTPase 1 | 21.9 | 1.2 | 18.7 |
| IFI203 | BC008167 | interferon activated gene 203 | 21.9 | 3.4 | 6.4 |
| ISG20 | BC022751 | interferon stimulated exonuclease gene 20 kDa | 20.9 | 3.4 | 6.1 |
| SECTM1 | BC010462 | secreted and transmembrane 1 | 17.7 | 1.2 | 15.0 |
| CCL13 | AF065933 | chemokine (C-C motif) ligand 13 | 16.8 | 5.8 | 2.9 |
| RSAD2 | NM_021384 | radical S-adenosyl methionine domain containing 2 | 15.5 | 7.8 | 2.0 |
| ZBP1 | NM_021394 | Z-DNA binding protein 1 | 15.4 | 4.2 | 3.7 |
| CCL4 | AF128218 | chemokine (C-C motif) ligand 4 | 15.1 | 8.1 | 1.9 |
| IL15RA | NM_133836 | interleukin 15 receptor, alpha | 14.9 | 3.3 | 4.5 |
| IGTP | NM_018738 | interferon gamma induced GTPase | 13.7 | 1.2 | 11.2 |
| OAS1B | BC012877 | 2'-5' oligoadenylate synthetase 1B | 12.7 | 2.1 | 6.2 |
| USP18 | NM_011909 | ubiquitin specific peptidase 18 | 11.6 | 1.0 | 11.4 |
| CD86 | NM_019388 | CD86 molecule | 11.1 | 6.0 | 1.8 |
| GBP6 | BC010229 | guanylate binding protein family, member 6 | 10.8 | 6.8 | 1.6 |
| FGL2 | BF136544 | fibrinogen-like 2 | 10.6 | 3.6 | 2.9 |
| CD40 | AI385482 | CD40 molecule, TNF receptor superfamily member 5 | 10.3 | 1.3 | 7.9 |
| TREX1 | NM_011637 | three prime repair exonuclease 1 | 10.2 | 5.2 | 2.0 |
| IFIH1 | AY075132 | interferon induced with helicase C domain 1 | 10.1 | 7.0 | 1.4 |
| CCL7 | AF128193 | chemokine (C-C motif) ligand 7 | 9.6 | 2.9 | 3.2 |
| C9ORF26 | NM_133775 | chromosome 9 open reading frame 26 (NF-HEV) | 9.1 | 4.4 | 2.1 |
| PVRL4 | AK004821 | poliovirus receptor-related 4 | 9.0 | 4.3 | 2.1 |
| TLR3 | NM_126166 | toll-like receptor 3 | 8.8 | 1.3 | 6.8 |
| RGC32 | NM_025427 | response gene to complement 32 | 8.7 | 3.0 | 2.9 |
| TRIM21 | BC010580 | tripartite motif-containing 21 | 8.4 | 2.6 | 3.2 |
| DAXX | NM_007829 | death-associated protein 6 | 7.9 | 1.6 | 4.9 |
| ABCB1 | M30697 | ATP-binding cassette, sub-family B (MDR/TAP), member 1 | 7.9 | 7.1 | 1.1 |
| GBP4 | NM_018734 | guanylate binding protein 4 | 7.5 | 4.6 | 1.6 |
| IL15 | NM_008357 | Interleukin 15 | 7.2 | 1.7 | 4.3 |
| TNF | NM_013693 | tumor necrosis factor (TNF superfamily, member 2) | 6.9 | 1.4 | 5.0 |
| IRF1 | NM_008390 | interferon regulatory factor 1 | 6.9 | 1.2 | 5.9 |
| CITED2 | NM_010828 | Cbp/p300-interacting transactivator, with Glu/Asp-rich carboxy-terminal domain, 2 | 6.8 | 1.5 | 4.6 |
| TPST1 | NM_013837 | tyrosylprotein sulfotransferase 1 | 6.7 | 6.1 | 1.1 |
| IRGM | NM_008326 | immunity-related GTPase family, M | 6.6 | 2.3 | 2.9 |
| NT5C3 | AV037573 | 5'-nucleotidase, cytosolic III | 6.4 | 1.8 | 3.6 |
| CCND2 | AV310588 | cyclin D2 | 6.4 | 2.0 | 3.2 |
| LGP2 | AF316999 | likely ortholog of mouse D11Igp2 | 6.4 | 2.7 | 2.4 |
| PVRL2 | BC009088 | poliovirus receptor-related 2 (herpesvirus entry mediator B) | 6.4 | 3.1 | 2.1 |
| IFI205 | M74124 | interferon activated gene 205 | 6.4 | 1.8 | 3.5 |
| CD274 | NM_021893 | CD274 molecule | 6.0 | 1.0 | 5.9 |
| PELI1 | NM_023324 | pellino homolog 1 (*Drosophila*) | 5.9 | 4.3 | 1.4 |
| GYPC | BC027408 | glycophorin C (Gerbich blood group) | 5.9 | 4.4 | 1.3 |
| 5830484A20RIK | AU017788 | RIKEN cDNA 5830484A20 gene | 5.7 | 4.0 | 1.4 |
| ARL4C | BI964400 | ADP-ribosylation factor-like 4C | 5.7 | 5.5 | 1.0 |
| CCRN4L | AF199491 | CCR4 carbon catabolite repression 4-like (*S. cerevisiae*) | 5.7 | 1.6 | 3.6 |
| CCL3 | NM_011337 | chemokine (C-C motif) ligand 3 | 5.6 | 1.4 | 4.1 |
| CCL5 | NM_013653 | chemokine (C-C motif) ligand 5 | 5.3 | 3.7 | 1.4 |
| PTX3 | NM_008987 | pentraxin-related gene, rapidly induced by IL-1 beta | 5.3 | 1.3 | 4.0 |
| PPP1R15A | NM_008654 | protein phosphatase 1, regulatory (inhibitor) subunit 15A | 5.3 | 1.6 | 3.4 |

TABLE 2-continued

Genes Up- or Down-Regulated ≥3-Fold Following
Treatment of Murine Macrophages with DMXAA[a]

| Gene Symbol | GenBank Accession Number | Description | Fold Change: BL/6[b] | Fold Change: IFNβ[−/−c] | WT/ KO[d] |
|---|---|---|---|---|---|
| TNFSF9 | NM_009404 | tumor necrosis factor (ligand) superfamily, member 9 | 5.1 | 1.7 | 3.0 |
| GBP2 | NM_010260 | guanylate binding protein 2, interferon-inducible | 4.8 | 1.6 | 3.1 |
| MAFK | NM_010757 | v-maf musculoaponeurotic fibrosarcoma oncogene homolog K (avian) | 4.7 | 1.6 | 3.0 |
| MARCH5 | AK009364 | membrane-associated ring finger (C3HC4) 5 | 4.7 | 1.9 | 2.5 |
| NMI | BC002019 | N-myc (and STAT) interactor | 4.5 | 1.6 | 2.9 |
| IL12B | NM_008352 | interleukin 12B (natural killer cell stimulatory factor 2, cytotoxic lymphocyte maturation factor 2, p40) | 4.4 | 1.4 | 3.2 |
| IFI16 | NM_008329 | interferon, gamma-inducible protein 16 | 4.3 | 2.7 | 1.6 |
| P4HA1 | AI314028 | procollagen-proline, 2-oxoglutarate 4-dioxygenase (proline 4-hydroxylase), alpha polypeptide I | 4.3 | 3.4 | 1.2 |
| TRIM25 | AI746456 | tripartite motif-containing 25 | 4.2 | 2.3 | 1.8 |
| ARHGEF3 | BC012262 | Rho guanine nucleotide exchange factor (GEF) 3 | 4.2 | 2.1 | 2.1 |
| TLK2 | NM_011903 | tousled-like kinase 2 | 4.2 | 1.4 | 3.0 |
| MOV10 | NM_008619 | Mov10, Moloney leukemia virus 10, homolog (mouse) | 4.2 | 1.2 | 3.4 |
| NP | AK008143 | nucleoside phosphorylase | 4.1 | 1.7 | 2.5 |
| IRF2 | NM_008391 | interferon regulatory factor 2 | 4.1 | 1.2 | 3.5 |
| PARP9 | NM_030253 | poly (ADP-ribose) polymerase family, member 9 | 4.0 | 1.4 | 2.8 |
| BAMBI | AF153440 | BMP and activin membrane-bound inhibitor homolog (Xenopus laevis) | 4.0 | 1.5 | 2.7 |
| SDC4 | BC005679 | syndecan 4 (amphiglycan, ryudocan) | 3.9 | 3.3 | 1.2 |
| SAP30 | NM_021788 | Sin3A-associated protein, 30 kDa | 3.9 | 1.6 | 2.4 |
| PLAU | X02389 | plasminogen activator, urokinase | 3.9 | 2.3 | 1.7 |
| STAT2 | AF088862 | signal transducer and activator of transcription 2, 113 kDa | 3.9 | 1.7 | 2.3 |
| CDC6 | NM_011799 | CDC6 cell division cycle 6 homolog (S. cerevisiae) | 3.8 | 3.2 | 1.2 |
| P8 | NM_019738 | p8 protein (candidate of metastasis 1) | 3.7 | 1.3 | 2.9 |
| ASF1A | AK007804 | ASF1 anti-silencing function 1 homolog A (S. cerevisiae) | 3.7 | 2.1 | 1.8 |
| IFI35 | BC008158 | interferon-induced protein 35 | 3.6 | 1.1 | 3.3 |
| SLC7A2 | M62838 | solute carrier family 7 (cationic amino acid transporter, y+ system), member 2 | 3.6 | 1.8 | 2.0 |
| SOAT1 | BC025091 | sterol O-acyltransferase (acyl-Coenzyme A: cholesterol acyltransferase) 1 | 3.6 | 1.9 | 1.8 |
| AFTIPHILIN | BC004630 | aftiphilin protein | 3.5 | 1.2 | 3.0 |
| APOBEC3F | NM_030255 | apolipoprotein B mRNA editing enzyme, catalytic polypeptide-like 3F | 3.5 | 1.4 | 2.5 |
| VCAM1 | NM_011693 | vascular cell adhesion molecule 1 | 3.4 | 1.6 | 2.1 |
| DSCR1 | AF282255 | Down syndrome critical region gene 1 | 3.4 | 2.7 | 1.3 |
| TMOD3 | AK017725 | tropomodulin 3 (ubiquitous) | 3.4 | 2.3 | 1.5 |
| TRIM34 | AF220142 | tripartite motif-containing 34 | 3.3 | 1.9 | 1.7 |
| RIPK2 | NM_138952 | receptor-interacting serine-threonine kinase 2 | 3.2 | 1.3 | 2.5 |
| SAV1 | BC019377 | salvador homolog 1 (Drosophila) | 3.2 | 2.6 | 1.2 |
| ZNF313 | AF502145 | zinc finger protein 313 | 3.2 | 1.5 | 2.1 |
| BID | NM_007544 | BH3 interacting domain death agonist | 3.2 | 2.9 | 1.1 |
| CCNE1 | NM_007633 | cyclin E1 | 3.2 | 2.9 | 1.1 |
| AKAP12 | NM_031185 | A kinase (PRKA) anchor protein (gravin) 12 | 3.2 | 1.5 | 2.2 |
| KATNA1 | AK012319 | katanin p60 (ATPase-containing) subunit A 1 | 3.2 | 1.5 | 2.1 |
| TOR1AIP1 | BC010841 | torsin A interacting protein 1 | 3.1 | 1.3 | 2.4 |
| CDKN1A | NM_007669 | cyclin-dependent kinase inhibitor 1A (p21, Cip1) | 3.1 | 1.1 | 2.7 |

TABLE 2-continued

Genes Up- or Down-Regulated ≥3-Fold Following
Treatment of Murine Macrophages with DMXAA[a]

| Gene Symbol | GenBank Accession Number | Description | Fold Change: BL/6[b] | Fold Change: IFNβ[−/−][c] | WT/ KO[d] |
|---|---|---|---|---|---|
| REL | NM_009044 | v-rel reticuloendotheliosis viral oncogene homolog (avian) | 3.1 | 1.1 | 2.8 |
| FGD6 | NM_053072 | FYVE, RhoGEF and PH domain containing 6 | 3.0 | 2.0 | 1.5 |
| ADRB2 | AV083350 | adrenergic, beta-2-, receptor, surface | −3.2 | 1.7 | 1.9 |
| CEBPB | AB012278 | CCAAT/enhancer binding protein (C/EBP), beta | −3.3 | 1.9 | 1.7 |
| CDC7 | AB018574 | CDC7 cell division cycle 7 (S. cerevisiae) | −3.4 | 1.6 | 2.2 |
| BHLHB2 | NM_011498 | basic helix-loop-helix domain containing, class B, 2 | −3.8 | 1.3 | 3.0 |
| CDC37L1 | BE824561 | CDC37 cell division cycle 37 homolog (S. cerevisiae)-like 1 | −3.8 | 2.2 | 1.7 |
| APBB1IP | BC023110 | amyloid beta (A4) precursor protein-binding, family B, member 1 interacting protein | −3.9 | 1.8 | 2.2 |
| AMPD3 | D85596 | adenosine monophosphate deaminase (isoform E) | −3.9 | 2.7 | 1.5 |
| ARID3A | NM_007880 | AT rich interactive domain 3A (BRIGHT-like) | −4.1 | 2.5 | 1.6 |
| ATRX | BB648845 | alpha thalassemia/mental retardation syndrome X-linked (RAD54 homolog, S. cerevisiae) | −4.2 | 2.6 | 1.6 |
| ACVR1B | BQ043509 | activin A receptor, type IB | −4.5 | 2.3 | 1.9 |
| CREBBP | BG076163 | CREB binding protein (Rubinstein-Taybi syndrome) | −4.5 | 6.3 | 0.7 |
| CLCA1 | AF047838 | chloride channel, calcium activated, family member 1 | −4.8 | 1.9 | 2.5 |
| CD37 | BC004610 | CD37 molecule | −5.2 | 1.1 | 4.7 |
| CYP1A2 | NM_009993 | cytochrome P450, family 1, subfamily A, polypeptide 2 | −7.0 | 3.9 | 1.8 |
| 2310043N10RIK | AK018202 | RIKEN cDNA 2310043N10 gene | −7.1 | 2.2 | 3.2 |
| BCL2 | NM_009741 | B-cell CLL/lymphoma 2 | −7.5 | 1.4 | 5.4 |
| ABL1 | J02995 | v-abl Abelson murine leukemia viral oncogene homolog 1 | −8.4 | 1.5 | 5.6 |
| B3GAT3 | BB634613 | beta-1,3-glucuronyltransferase 3 (glucuronosyltransferase I) | −9.0 | 1.6 | 5.5 |
| CNR2 | NM_009924 | cannabinoid receptor 2 (macrophage) | −9.1 | 2.3 | 4.0 |
| ABLIM1 | BG065289 | actin binding LIM protein 1 | −9.7 | 1.4 | 7.1 |
| AP2A2 | AK009735 | adaptor-related protein complex 2, alpha 2 subunit | −10.1 | 8.8 | 1.1 |
| CCNF | NM_007634 | cyclin F | −10.6 | 2.4 | 4.4 |
| BACE1 | AK014390 | beta-site APP-cleaving enzyme 1 | −11.5 | 3.7 | 3.2 |
| BCL2L1 | U10100 | BCL2-like 1 | −14.0 | 2.3 | 6.0 |
| C8ORF4 | BC016562 | chromosome 8 open reading frame 4 | −35.4 | 4.1 | 8.7 |
| CYP1B1 | BI251808 | cytochrome P450, family 1, subfamily B, polypeptide 1 | −44.3 | 5.9 | 7.5 |

[a]Peritoneal macrophages were stimulated with DMXAA or medium alone for 3 h. Total RNA was isolated and used as starting material for microarray analysis. A ≥3-fold increase or decrease between inducible and basal mRNA levels was set as the criteria for inclusion of a gene as modulated.
[b]Values reflect the fold change in DMXAA-treated wild-type cells vs. unstimulated wild-type cells.
[c]Values reflect the fold change in DMXAA-treated IFN-β-deficient cells vs. unstimulated wild-type cells.
[d]Ratio of fold change in DMXAA-treated wild-type vs. IFN-β-deficient cells.

EXAMPLE 4

DMXAA Activation of IRF-3

The IRF family of transcription factors has been shown to be integral to the regulation of the type I IFN response (see, for example, Schafer, S. L. et al. (1998) "Regulation Of Type I Interferon Gene Expression By Interferon Regulatory Factor-3," J. Biol. Chem. 273:2714-2720, and Honda, K. et al. (2005) "IRF-7 Is The Master Regulator Of Type-I Interferon-Dependent Immune Responses," Nature 434:772-777). Phosphorylation of IRF-3 leads to the formation of IRF-3 dimers, followed by the nuclear translocation and transcription of genes like IFN-β and RANTES (see, for example, Au, W. C. et al. (1995) "Identification Of A Member Of The Interferon Regulatory Factor Family That Binds To The Interferon-Stimulated Response Element And Activates Expression Of Interferon-Induced Genes," Proc. Natl. Acad. Sci. (U.S.A.) 92:11657-11661). To study the capacity of DMXAA to activate IRF-3, cell lysates from peritoneal macrophages exposed to either LPS or DMXAA were subjected to native PAGE to preserve fragile IRF-3 dimers. Proteins were transferred to PVDF and subjected to Western analysis with an anti-IRF-3 antibody. FIG. 3A demonstrates that activated IRF-3 dimers are much more abundant and longer-lived in DMXAA- vs. LPS-stimulated macrophages.

The robust activation of IRF-3 in DMXAA-stimulated macrophages led the inventors to investigate whether IRF-3 was an absolute requirement for activation of cells by DMXAA. To address this possibility, peritoneal macrophages from wild-type and IRF-3$^{-/-}$ mice were cultured in medium only or DMXAA. Supernatants collected at 24 h were analyzed for cytokine production. FIG. 3B shows that, consistent with the robust IRF-3 activation observed in DMXAA-treated cells, IRF-3$^{-/-}$ macrophages fail to produce RANTES, the product of a known IRF-3-dependent gene (see, for example, Lin, R. et al. (1999) "*Essential Role Of Interferon Regulatory Factor* 3 *In Direct Activation Of RANTES Chemokine Transcription,*" Mol. Cell. Biol. 19:959-966). Surprisingly, secretion of TNF-α was also reduced to background levels in IRF-3-deficient macrophages. To evaluate further the role of activated IRF-3 in DMXAA-induced signaling, the inventors exposed MEFs lacking TBK1 to medium only, LPS, or DMXAA and measured gene expression. LPS-stimulated TBK1-deficient MEFs produce wild-type levels of RANTES and TNF-α mRNA (FIG. 3C). However, TBK1$^{-/-}$ MEFs fail to express either RANTES or TNF-α mRNA in response to DMXAA. Collectively, these data support the conclusion that DMXAA activates an IRF3-dependent pathway that is dependent on the known IRF-3 kinase, TBK1.

EXAMPLE 5

Figures 4A, 4B, 4C, 4D:
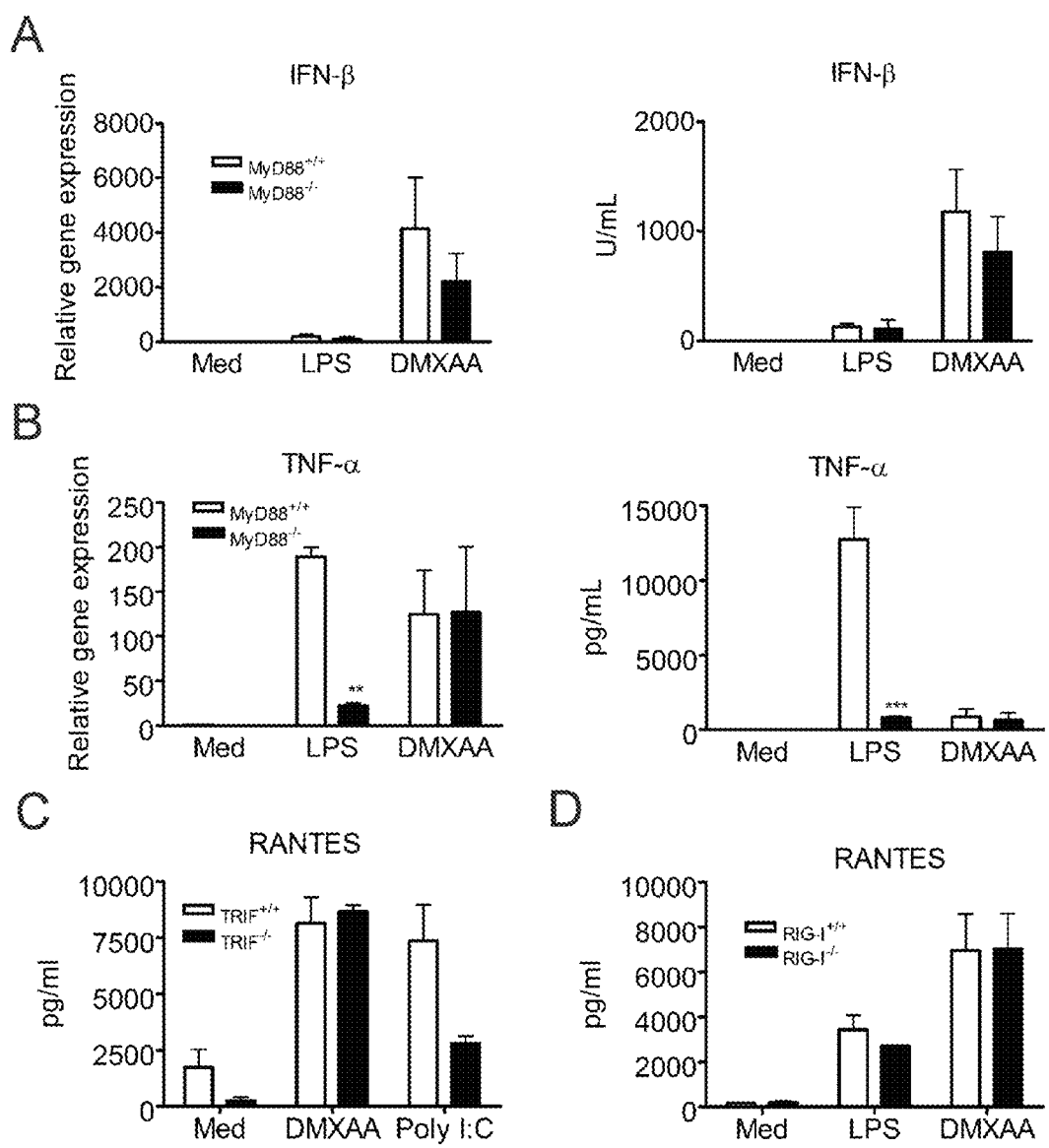
FIGS. 4A, 4B, 4C and 4D show the effect of DMXAA on MyD88-, TRIF-, and RIG-I-induced gene expression in peritoneal macrophages from MyD88$^{+/+}$ or MyD88$^{-/-}$ mice that were stimulated with medium alone, LPS (100 ng/ml), or DMXAA (100 µg/ml) for 2 h for mRNA detection (left panels) or for 24 h for protein detection (right panels) (FIGS. 4A and 4B), TRIF$^{+/+}$ and TRIF$^{-/-}$ MEFs that were stimulated with medium alone, LPS (100 ng/ml), or DMXAA (100 µg/ml) for 24 h (FIG. 4C), and RIG-I$^{+/+}$ and RIG-I$^{-/-}$ MEFs that were stimulated with medium alone, LPS (100 ng/ml), or DMXAA (100 µg/ml) for 24 h (FIG. 4D). Results represent the mean±SE for ≥3 separate experiments. , $p<0.01$; *, $p<0.001$.

DMXAA Induction of Gene Expression Via an MyD88-, TRIF-, and RIG-I-Independent Pathway The inventors tested the ability of DMXAA to induce signaling in MyD88$^{-/-}$ macrophages. As shown in FIG. 4A, and previously reported (see, for example, Kawai, T. et al. (1999) "*Unresponsiveness Of MyD88-Deficient Mice To Endotoxin,*" Immunity 11:115-122, and Toshchakov, V. et al. (2002) "*TLR4, But Not TLR2, Mediates IFN-Beta-Induced STAT1alpha/Beta-Dependent Gene Expression In Macrophages,*" Nature Immunol. 3:392-398), LPS-induced IFN-β mRNA and protein are not significantly decreased by MyD88 deficiency, whereas levels of TNF-α are dramatically inhibited in the MyD88$^{-/-}$ macrophages (FIG. 4B). In contrast, DMXAA-induced IFN-β and TNF-α mRNA and protein are not significantly altered in the absence of MyD88. These data further support the notion that genes commonly associated with the "MyD88-independent" pathway are selectively upregulated by DMXAA and, importantly, MyD88 does not contribute to signaling induced by DMXAA.

TLRs 3 and 4 share the ability to activate IRF-3 and induce IFN-β via another adapter called TRIF. To address whether DMXAA utilizes the MyD88-independent pathway mediated by TRIF, background-matched, wild-type and TRIF$^{-/-}$ MEFs were stimulated with DMXAA or the TLR3 agonist, poly I:C. FIG. 4C illustrates that, compared to poly I:C, a known TRIF-dependent inducer of RANTES (see, for example, Yamamoto, M. et al. (2002) "*Cutting Edge: A Novel Toll/IL-1 Receptor Domain-Containing Adapter That Preferentially Activates The IFN-Beta Promoter In The Toll-Like Receptor Signaling,*" J. Immunol. 169:6668-6672), DMXAA-induced RANTES is unaffected by the absence of TRIF. Together, these data indicate that DMXAA signals independently of MyD88 and TRIF. These results, in combination with the results from the study in TLR4$^{-/-}$ macrophages (FIG. 2E), indicate that none of the known TLRs serve as a receptor for DMXAA because all of them require MyD88 and/or TRIF to mediate signaling.

Because the inventors' data implied that DMXAA does not require known TLRs to activate IRF-3-inducible genes, the inventors explored whether DMXAA might engage the recently identified cytosolic RNA helicase, RIG-I. Therefore, background-matched wild-type MEFs were first compared to RIG-I$^{-/-}$ MEFs, which failed to respond to Newcastle Disease Virus. However, as shown in FIG. 4D, when stimulated with LPS and DMXAA, RANTES secretion is intact in the RIG-I$^{-/-}$ MEFs. Thus, DMXAA-activated IRF-3 and IRF-3-dependent gene expression is RIG-1-independent.

EXAMPLE 6

Induction of Cross-Tolerance by LPS or DMXAA

Endotoxin tolerance is a poorly understood phenomenon that has been described as a transient state of LPS-hyporesponsiveness induced by prior exposure to a low level of LPS both in vitro in macrophages and in vivo. Moreover, "TLR heterotolerance" can be induced (i.e., prior exposure to one TLR agonist diminishes responsiveness to challenge through a distinct TLR (see, for example, Dobrovolskaia, M. A. et al. (2003) "*Induction Of In Vitro Reprogramming By Toll-Like Receptor (TLR)2 And TLR4 Agonists In Murine Macrophages: Effects Of TLR "Homotolerance" Versus "Heterotolerance" On NF-Kappa B Signaling Pathway Components,*" J. Immunol. 170:508-519) and that LPS and IL-1α "cross-tolerize" (see, for example, Medvedev, A. E. et al. (2000) "*Inhibition Of Lipopolysaccharide-Induced Signal Transduction In Endotoxin-Tolerized Mouse Macrophages: Dysregulation Of Cytokine, Chemokine, And Toll-Like Receptor* 2 *And* 4 *Gene Expression,*" J. Immunol. 164:5564-5574). The ability to induce heterotolerance or cross-tolerance has been suggested to be due to disruption of shared signaling pathway molecules between distinct receptor systems (see, for example, Dobrovolskaia, M. A. et al. (2003) "*Induction Of In Vitro Reprogramming By Toll-Like Receptor (TLR)2 And TLR4 Agonists In Murine Macrophages: Effects Of TLR "Homotolerance" Versus "Heterotolerance" On NF-Kappa B Signaling Pathway Components,*" J. Immunol. 170:508-519). To determine if LPS and DMXAA cross-tolerize, the inventors pretreated peritoneal macrophages with medium, LPS, or DMXAA. After 24 h, cells were washed, and restimulated for 1 h with LPS or DMXAA. Protein was subjected to native PAGE and Western blotting for IRF-3 and IFN-β mRNA was quantified by real-time PCR.

Figures 5A, 5B:
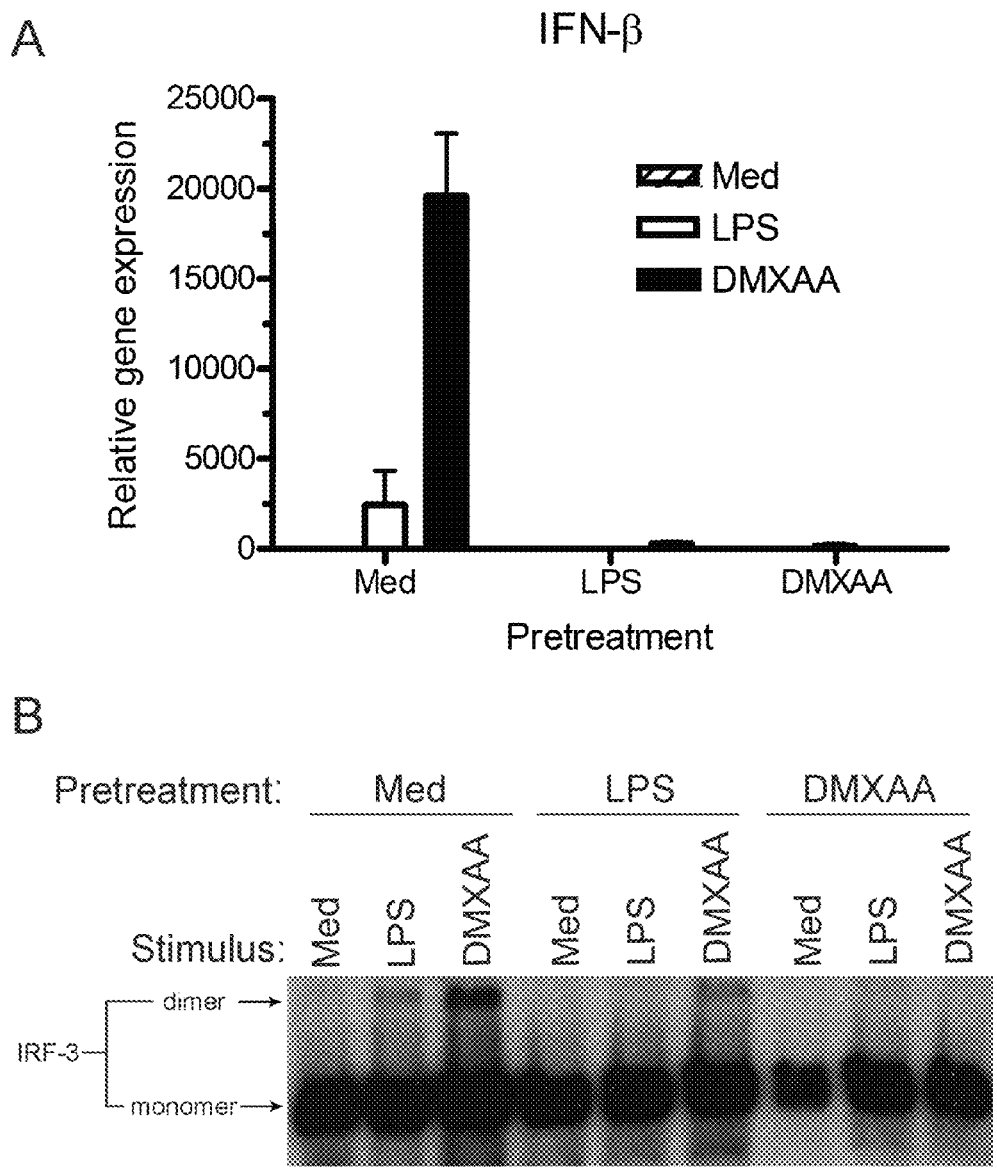
FIGS. 5A and 5B show the effect of DMXAA pretreatment of macrophages on the induction of a state of refractoriness upon re-exposure to either LPS or DMXAA. Total RNA (FIG. 5A) or protein (FIG. 5B) from C57BL/6 peritoneal macrophages that were pretreated with medium alone, LPS (100 ng/ml), or DMXAA (100 µg/ml), washed, and restimulated with medium, LPS, or DMXAA was collected subjected to quantitative real-time PCR (FIG. 5A) or native-PAGE followed by Western blotting for IRF-3 (FIG. 5B). Results shown are mean±SE of a single representative experiment (N=3).

LPS-pretreatment of cells results in a diminished response to a second LPS exposure, both at the level of IFN-β mRNA (FIG. 5A) and IRF-3 dimerization (FIG. 5B), indicating that classical endotoxin tolerance is induced. LPS pretreatment of macrophages also mitigates the subsequent response to DMXAA. Conversely, pretreatment with DMXAA induces a state of refractoriness to restimulation with either LPS or DMXAA. These results indicate that signaling elements rendered hypoactive by pretreatment with LPS are also utilized by DMXAA and vice versa.

EXAMPLE 7

Selective Inhibition of DMXAA-Induced IFN-β by Salicylic Acid

Figure 6A:
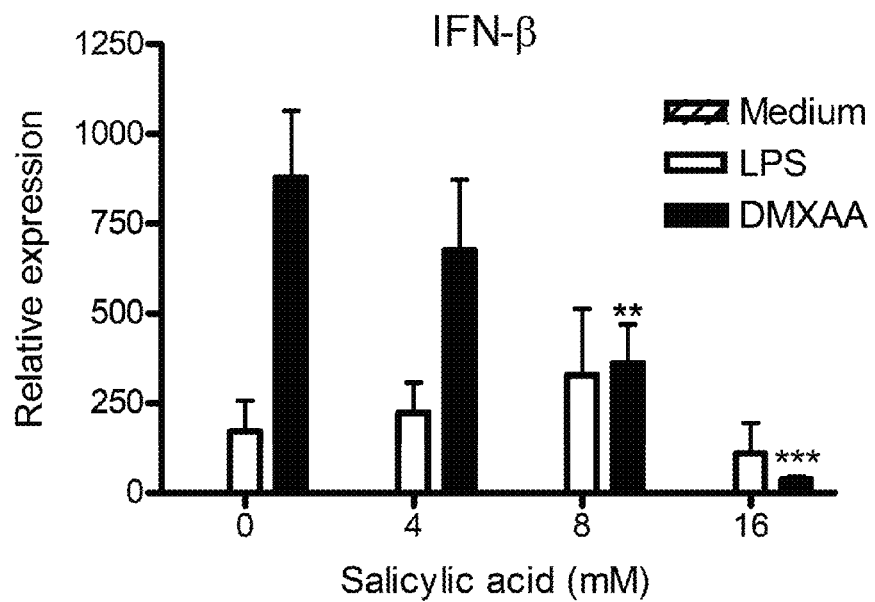
FIGS. 6A and 6B show the effect of salicylic acid (SA) on DMXAA-induced gene expression (FIG. 6A) and IRF-3 activation (FIG. 6B) in peritoneal macrophages from C57BL/6 mice that were pretreated with medium alone or 16 mM SA for 1 h, followed by stimulation with medium alone, LPS (100 ng/ml), or DMXAA (100 µg/ml) for an additional 1 h. Results represent mean±SE of ≥3 separate experiments. , $p<0.01$; *, $p<0.001$.
Figure 6B:
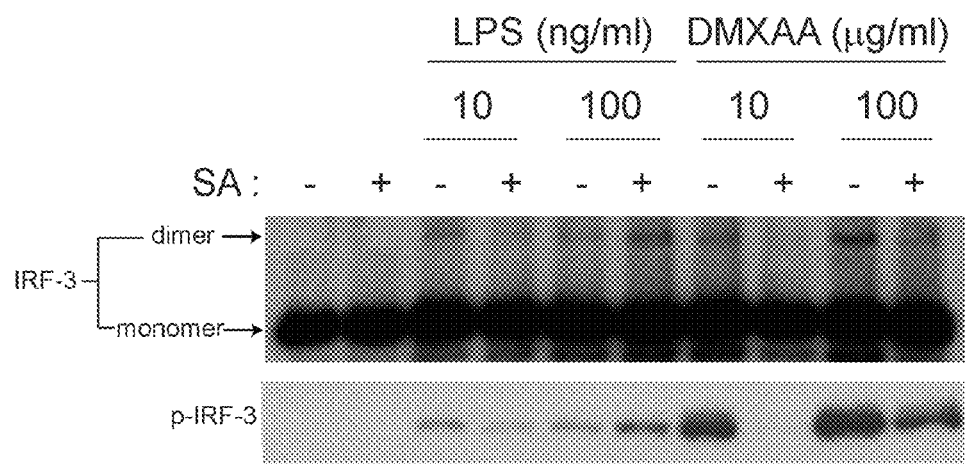

SA has been reported to inhibit IκB kinase β (IKKβ) (see, for example, Kopp, E. et al. (1994) "*Inhibition Of NF-Kappa B By Sodium Salicylate And Aspirin,*" Science 265:956-959, and Yin, M. J. et al. (1998) "*The Anti-Inflammatory Agents Aspirin And Salicylate Inhibit The Activity Of I(Kappa)B Kinase-Beta,*" Nature 396:77-80) and has been shown to inhibit DMXAA-induced TNF-α in human mononuclear cells when DMXAA is combined with anti-CD14 antibodies or deacylated LPS (Philpott, M. et al. (2001) "*The Antitumour Agent 5,6-Dimethylxanthenone-4-Acetic Acid Acts In Vitro On Human Mononuclear Cells As A Co-Stimulator With Other Inducers Of Tumour Necrosis Factor*," Eur. J. Canc. 37:1930-1937). Because IRF-3-dependent gene expression has not previously been shown to be SA-sensitive, the inventors tested whether SA might down-regulate DMXAA-induced IFN-β expression. The inventors pretreated peritoneal macrophages with increasing concentrations of SA, followed by stimulation with LPS or DMXAA. FIG. 6A shows that SA dramatically reduces DMXAA-induced IFN-β expression, while LPS-induced IFN-β mRNA expression was essentially unaffected. Furthermore, pretreatment of macrophages with SA also inhibits both IRF-3 dimer formation and phosphorylation of serine 396 in response to DMXAA, but not LPS (FIG. 6B). These data indicate that SA inhibits a TBK1-dependent pathway that leads to the induction of IFN-β that is also preferentially activated by DMXAA.

EXAMPLE 8

MAVS-Independent Rantes Production

Figure 7:
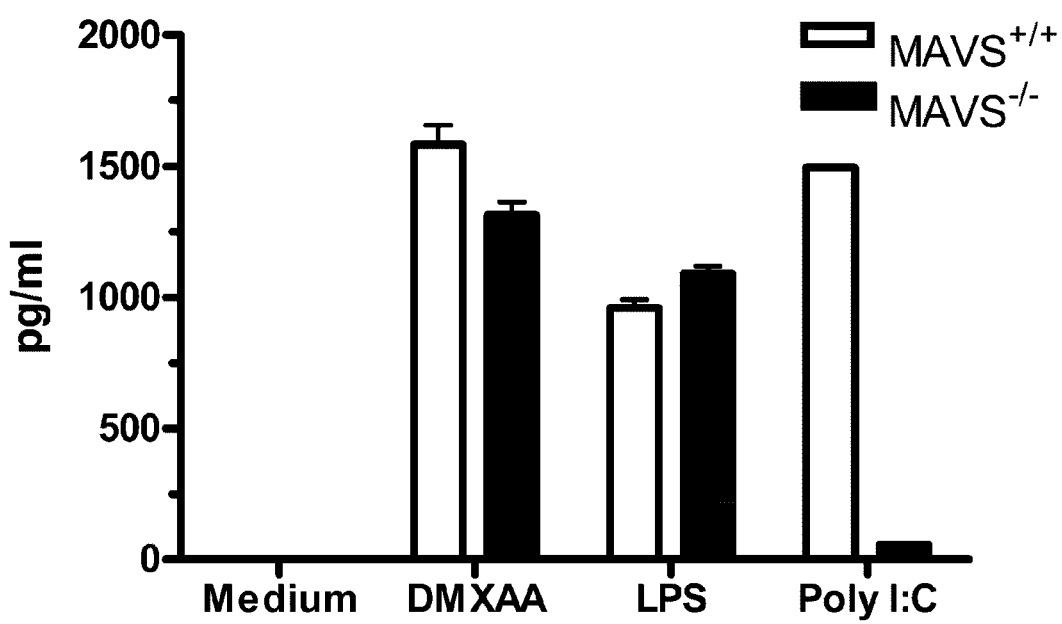
FIG. 7 shows the production of RANTES protein in MAVS$^{+/+}$ and MAVS$^{-/-}$ MEFs that were treated with medium alone, DMXAA (100 µg/ml), LPS (100 µg/ml), or poly (I:C) (10 µg/ml) for 24 h.

MAVS has been shown to be a critical adapter molecule involved in signal transduction from both known cytosolic RNA helicases (RIG-I and Mda5). FIG. 7 shows that DMXAA induces RANTES via a MAVS-independent pathway. MAVS deficiency completely abrogates cellular responses to RNA virus infection (or, as in this case, transfected poly I:C, which is a reliable and widely accepted proxy for cytosolic virus replication). MAVS-deficient cells are highly susceptible to infection by a wide variety of viruses. Because all known signaling cascades originating from either RIG-I or Mda5 funnel through MAVS, the finding that DMXAA does not require MAVS implies that the cytosolic RNA helicases do not play a role in the response to DMXAA.

EXAMPLE 9

Antibacterial Activity of DMXAA

The antibacterial activity of DMXAA was demonstrated by showing that DMXAA activated murine macrophages to kill intracellular *Francisella tularensis* LVS, a bacterium that replicates both intracellularly within macrophages, and extracellularly. Since IFN-β is involved in the control of *Francisella tularensis* (Ft) LVS replication within murine macrophages, the efficacy of DMXAA as an antibacterial compound (mediated by macrophage-derived IFN-β) was tested by determining its affect on *Francisella tularensis* (Ft) LVS replication.

Figure 8:
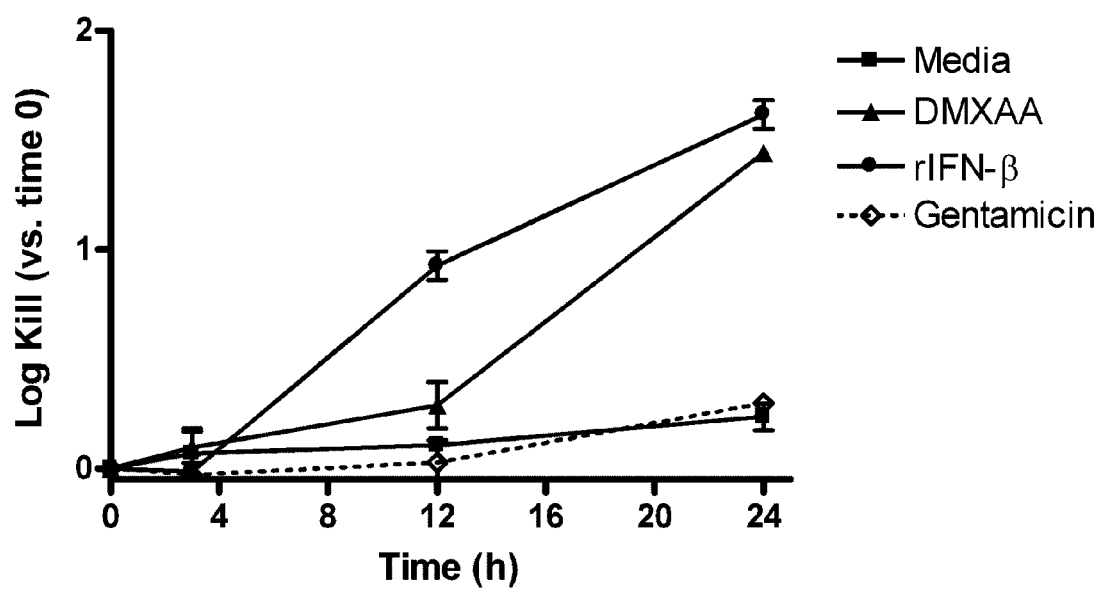
FIG. 8 illustrates the antibacterial activity of DMXAA. Macrophages were infected with wild-type (WT) Ft LVS at an MOI of 10-20 for 2 hr. After washing twice with PBS, infected cells were incubated for 1 hr in media containing 50 µg/ml gentamicin (Sigma-Aldrich). Gentamicin was added to the medium to kill the extracellular bacterium, and thus the number of bacteria quantified represents those that have replicated intracellularly. After treatment with gentamicin to kill the extracellular bacteria, cells were washed twice with PBS and media or media supplemented with 2 µg/ml gentamicin, 100 µg/ml DMXAA or 100 U/ml rIFN-β was added to the cells. This addition of media was defined as the zero time point. To enumerate the number of intracellular colony forming units (CFU), cells were first washed twice with PBS then 1 ml of ice-cold 0.02% SDS (Teknova) in PBS was added to lyse the macrophages. Lysates were serially diluted and plated on Mueller-Hinton (MH) agar plates. "Log kill" represents the difference between the log of the number of bacteria recovered at any time point and the log of the average number of bacteria recovered at time zero.

Thioglycollate-elicited C57BL/6 murine macrophages were infected with Ft LVS for 2 hr, treated with gentamycin to kill any extracellular bacteria, and subsequently treated with 100 U/ml rIFN-β, 100 µg/ml DMXAA, gentimicin, or media alone. DMXAA treatment of Ft LVS-infected macrophages was found to reduce bacterial burden 10-fold within 24 hr, to the level induced by exogenous rIFN-β. This impact on bacterial burden was mediated through DMXAA's effect on macrophages as DMXAA alone (100 µg/ml) had no effect on Ft LVS replication over a 24 hr period. DMXAA took longer to reduce a bacterial burden than rIFN-β, presumably due to the time required to induce endogenous IFN-β. The results of these investigations are shown in FIG. 8.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for treating a viral pathogen infection in a mammal comprising administering to the mammal in need of such treatment a pharmaceutical composition comprising DMXAA (5,6-dimethylxanthenone-4-acetic acid) or

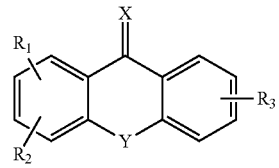

a pharmaceutically acceptable salt or ester thereof with a pharmaceutically acceptable acid; and
(B) one or more pharmaceutically acceptable carriers, diluents or excipients;
wherein the administered pharmaceutical composition is provided in a therapeutic amount sufficient to induce expression of IFN-β thereby providing an IFN-β-mediated anti-viral response, wherein the viral pathogen is an influenza virus.

2. The method of claim 1, wherein said virus infects respiratory tract, and said administration of said composition is to the respiratory system of said recipient mammal.

3. The method of claim 1, wherein DMXAA is administered in conjunction with a second compound, said second compound being a therapeutic agent.

4. A method of treating a mammal who has already been exposed to a viral pathogen comprising administering to the mammal in need of such treatment a pharmaceutical composition comprising DMXAA (5,6-dimethylxanthenone-4-acetic acid) or a pharmaceutically acceptable salt or ester thereof with a pharmaceutically acceptable acid; and
one or more pharmaceutical acceptable carriers, diluents or excipients;
wherein the administered pharmaceutical composition is provided in a prophylactic amount sufficient to induce expression of IFN-β thereby providing an IFN-β-mediated anti-viral response; and
wherein the viral pathogen is an influenza virus.

5. The method of claim 4, wherein said virus infects respiratory tract, and said administration of said composition is to the respiratory system of said recipient mammal.

6. The method of claim 4, wherein the mammal is selected from the group consisting of young children, immunocompromised individuals, travelers, military personnel, healthcare workers, and the elderly.

7. A method of treating a mammal who is at risk of infection by a viral pathogen comprising administering to the mammal in need of such treatment a pharmaceutical composition comprising DMXAA (5,6-dimethylxanthenone-4-acetic acid) or a pharmaceutically acceptable salt or ester thereof with a pharmaceutically acceptable acid;

and one or more pharmaceutically acceptable diluents or excipients;

wherein the administered pharmaceutical composition is provided in a prophylactic amount sufficient to induce expression of IFN-β thereby providing an IFN-β-mediated anti-viral response; and wherein the viral pathogen is an influenza virus, and wherein the mammal is selected from the group consisting of young children, travelers, military personnel, healthcare workers, and elderly.

* * * * *